US009506117B2

(12) United States Patent
Lyng et al.

(10) Patent No.: US 9,506,117 B2
(45) Date of Patent: Nov. 29, 2016

(54) METHODS AND BIOMARKERS FOR DETECTION AND PROGNOSIS OF CERVICAL CANCER

(71) Applicant: Olso universitetssykehus HF, Oslo (NO)

(72) Inventors: Heidi Lyng, Lommedalen (NO); Cathinka Halle Julin, Oslo (NO)

(73) Assignee: Oslo universitetssykehus HF, Oslo (NO)

( * ) Notice: Subject to any disclaimer, the term of this patent is extended or adjusted under 35 U.S.C. 154(b) by 142 days.

(21) Appl. No.: 14/379,585

(22) PCT Filed: Feb. 20, 2013

(86) PCT No.: PCT/IB2013/000664
§ 371 (c)(1),
(2) Date: Aug. 19, 2014

(87) PCT Pub. No.: WO2013/124738
PCT Pub. Date: Aug. 29, 2013

(65) Prior Publication Data
US 2015/0018242 A1    Jan. 15, 2015

Related U.S. Application Data

(60) Provisional application No. 61/601,194, filed on Feb. 21, 2012.

(51) Int. Cl.
*C12Q 1/68* (2006.01)
*G01N 33/574* (2006.01)

(52) U.S. Cl.
CPC ....... *C12Q 1/6886* (2013.01); *G01N 33/57411* (2013.01); *C12Q 2600/118* (2013.01); *C12Q 2600/158* (2013.01); *G01N 2800/7038* (2013.01)

(58) Field of Classification Search
None
See application file for complete search history.

(56) References Cited

U.S. PATENT DOCUMENTS

| | | | |
|---|---|---|---|
| 2006/0035244 A1* | 2/2006 | Riggins | C12Q 1/6886 435/6.18 |
| 2006/0211009 A1 | 9/2006 | An et al. | |
| 2007/0212360 A1* | 9/2007 | Denko | A61K 31/404 424/155.1 |
| 2010/0216131 A1* | 8/2010 | Luthra | C12Q 1/6886 435/6.11 |
| 2011/0224088 A1 | 9/2011 | Lyng et al. | |
| 2012/0329662 A1* | 12/2012 | West | C12Q 1/6809 506/7 |
| 2014/0026234 A1* | 1/2014 | Lisanti | G01N 33/574 800/10 |

FOREIGN PATENT DOCUMENTS

WO    2013/124738    8/2013

OTHER PUBLICATIONS

Sung et al., "Genome-wide expression analysis using microarray identified complex signaling pathways modulated by hypoxia in nasopharygeal carcinoma," Cancer Letters, 2007, 253, 74-88.
Koritzinsky et al. "The hypoxic proteome is influenced by gene-specific changes in mRNA translation," Radiotherapy and Oncology, 2005, 76, 177-186.
Halle, C. L., "Biomarers in chemotherapy of cervical cancer," 2012, pp. 1-80, p. 45, paragraph 4—p. 47, paragraph 25.
Grigsby, et al., "Comparison of Molecular Markers of Hypoxia and Imaging with 60Cu-ATSM in Cancer of the Uterine Cervix," Molecular Imaging and Biology, Springer-Verlag, NE, vol. 9, No. 5, 2007, pp. 278-283.
Le, et al., "Clinical biomarkers for hypoxia targeting," Cancer and Metastatis Reviews, Luwer Academic Publishers DO, vol. 27, No. 3, 2008, pp. 351-362.
Cooper, et al., "Tumour oxygenation levels correlate with dynamic contrast-enhanced magnetic resonance imaging parameters in carcinoma of the cervix," Radiotherapy and Oncology, vol. 57, No. 1, Oct. 1, 2000, pp. 53-59.
Airley, et al., "GLUT-1 and CAIX as intrinsic markers of hypoxia in carcinoma of the cervix: Relationship to pimonidazole binding," International Journal of Cancer, vol. 104, No. 1, 2003, pp. 85-91.
Balleyguier, C. et al., Staging of uterine cervical cancer with MRI: guidelines of the European Society of Urogenital Radiology. Eur Radiol 2010.
Follen, M. et al., Imaging in cervical cancer. Cancer 2003;98:2028-38.
Potter, R. et al., Clinical impact of MRI assisted dose volume adaptation and dose escalation in brachytherapy of locally advanced cervix cancer. Radiother Oncol 2007;83:148-55.
Loncaster, J.A. et al., Prediction of radiotherapy outcome using dynamic contrast enhanced MRI of carcinoma of the cervix. Int J Radiat Oncol Biol Phys 2002;54:759-67.
Hawighorst, H. et al., Angiogenic activity of cervical carcinoma: assessment by functional magnetic resonance imaging-based parameters and a histomorphological approach in correlation with disease outcome. Clin Cancer Res 1998;4:2305-12.
Gong, Q.Y. et al., Contrast enhanced dynamic MRI of cervical carcinoma during radiotherapy: early prediction of tumour regression rate. Br J Radiol 1999;72:1177-84.
Yamashita, Y. et al., Dynamic contrast-enhanced MR imaging of uterine cervical cancer: pharmacokinetic analysis with histopathologic correlation and its importance in predicting the outcome of radiation therapy. Radiology 2000;216:803-9.
Yuh, W.T. et al., Predicting control of primary tumor and survival by DCE MRI during early therapy in cervical cancer. Invest Radiol 2009;44:343-50.
Lyng, H. et al., Gene expressions and copy Nos. associated with metastatic phenotypes of uterine cervical cancer. BMC Genomics 2006;7:268.

(Continued)

*Primary Examiner* — Jim Ketter
(74) *Attorney, Agent, or Firm* — Casimir Jones, S.C.

(57) ABSTRACT

The present invention relates to methods and biomarkers for detection of cervical cancer in biological samples, and in particular to markers associated with hypoxia related to the cervical cancer.

13 Claims, 6 Drawing Sheets

(56) References Cited

OTHER PUBLICATIONS

Huang, L.E. et al., Activation of hypoxia-inducible transcription factor depends primarily upon redox-sensitive stabilization of its alpha subunit. J Biol Chem 1996;271:32253-9.

Chi, J.T. et al., Gene expression programs in response to hypoxia: cell type specificity and prognostic significance in human cancers. PLoS Med 2006;3:e47.

Hockel, M. et al., Association between tumor hypoxia and malignant progression in advanced cancer of the uterine cervix. Cancer Res 1996;56:4509-15.

Mense, S.M. et al., Gene expression profiling reveals the profound upregulation of hypoxia-responsive genes in primary human astrocytes. Physiol Genomics 2006;25:435-49.

Winter, S.C. et al., Relation of a hypoxia metagene derived from head and neck cancer to prognosis of multiple cancers. Cancer Res 2007;67:3441-9.

Fyles, A. et al., Tumor hypoxia has independent predictor impact only in patients with node-negative cervix cancer, 2002.

International Search Report and Written Opinion, International Patent Application No. PCT/IB2013/000664, mailed Nov. 14, 2013.

International Search Report and Written Opinion, International Patent Application No. PCT/IB2015/000567, mailed Jul. 29, 2015.

Farkas, S. et al., "Genome-wide DNA methylation assay reveals novel candidate biomarker genes in cervical cancer," Epigenetics, 2013, vol. 8, No. 11, pp. 1213-1225.

Zhuang J. et al., "A comparison of feature selection and classification methods in DNA methylation studies using the Illumina Infinium platform" BMC Bioinformatics, 2012, vol. 13, No. 1, p. 59.

Sartor M. et al, "Genome-wide methylation and expression differences in HPV(+) and HPV(−) squamous cell carcinoma cell lines are consistent with divergent mechanisms of carcinogenesis" Epigenetics, 2011, vol. 6, No. 6, pp. 777-787.

CN Office Action, CN Patent Application No. 201380017262.2, mailed Apr. 28, 2015, English translation included.

\* cited by examiner

METHODS AND BIOMARKERS FOR DETECTION AND PROGNOSIS OF CERVICAL CANCER

CROSS-REFERENCE TO RELATED APPLICATIONS

The present application is a Section 371 U.S. national stage entry of pending International Patent Application No. PCT/IB2013/000664, International Filing Date Feb. 20, 2013, which published on Aug. 29, 2013 as Publication No. WO 2013/124738, which claims the benefit of expired U.S. Provisional Patent Application No. 61/601,194, filed Feb. 21, 2012, the contents of which are incorporated by reference in its entirety.

FIELD OF THE INVENTION

The present invention relates to methods and biomarkers for detection of cervical cancer in biological samples, and in particular to markers associated with hypoxia related to the cervical cancer.

BACKGROUND OF THE INVENTION

Functional tumor imaging like dynamic contrast enhanced magnetic resonance imaging (DCE-MRI) can be used to obtain biological information about the cancer disease and thereby assess tumor aggressiveness. It has thus been proposed that these imaging techniques (DCE-MRI) may be useful tools in the clinic to stratify patients to different treatment regimes on the way to personalized therapy. In particular, patients treated with radiotherapy may benefit considerable from such an approach, due to the central role of imaging in the radiotherapy planning (1). A powerful strategy for future improvements in radiotherapy could be to link the discovery of molecular biomarkers of radioresistance to developments in functional imaging techniques (Coleman). PET and MRI are now indispensable tools in the handling of cancer patients to detect metastases and assess disease dissemination. However, their ability to visualize tumor biology and aggressiveness has not been utilized, mainly because it is not yet clear how to best extract the prognostic parameters nor their biological meaning from the images.

Several studies have recently demonstrated the potential in combining imaging data with gene expression data of the same tumors, to find valuable information about the background of various imaging parameters (15-21). However, there is still unexplored information embedded in the images which needs to be elucidated to be able to efficiently use DCE-MRI as a biomarker in cervical cancer.

SUMMARY OF THE INVENTION

The present invention relates to methods and biomarkers for detection of cervical cancer in biological samples, and in particular to markers associated with hypoxia.

In some embodiments, the present invention provides methods for predicting a predisposition to cervical cancer in a subject, diagnosing a cervical cancer in a subject, predicting the likelihood of recurrence of cervical cancer in a subject, providing a prognosis for a subject with cervical cancer, or selecting a subject with cervical cancer for treatment with a particular therapy, comprising: determining a patient hypoxia profile for a tissue or subsection of tissue from a patient; and comparing the patient hypoxia profile with a reference hypoxia profile, wherein an altered profile for the patient relative to the reference profile provides an indication selected from the group consisting of an indication of a predisposition of the subject to cervical cancer, an indication that the subject has cervical cancer, an indication of the likelihood of recurrence of the cervical cancer in the subject, an indication of survival of the subject, and indication of the aggressiveness of the cervical cancer, an indication of the likely outcome of treatment of the cervical cancer and an indication that the subject is a candidate for treatment with a particular therapy.

In some embodiments, the patient hypoxia profile is determined by measurement of the $A_{Brix}$ parameter using magnetic resonance imaging (MRI).

In some embodiments, the patient hypoxia profile is determined by: a) contacting a biological sample from a subject with at least one hypoxia profile informative reagent for detecting the level of expression of one or more hypoxia profile gene products; b) detecting the level of expression of the one or more hypoxia profile gene products using an in vitro assay, wherein an altered level of expression of the one or more genes provides an indication selected from the group consisting of an indication of a predisposition of the subject to cervical cancer, an indication that the subject has cervical cancer, an indication of the likelihood of recurrence of the cervical cancer in the subject, an indication of survival of the subject, and indication of the aggressiveness of the cervical cancer, an indication of the likely outcome of treatment of the cervical cancer and an indication that the subject is a candidate for treatment with a particular therapy.

In some embodiments, the altered level of expression is determined by comparison to a reference profile.

In some embodiments, the hypoxia profile is determined by detecting the expression level of gene products from at least one gene selected from the group consisting of ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1 using an in vitro assay and wherein the expression level of gene products from the at least five genes is compared with a reference expression level of the at least one gene. In some embodiments, the hypoxia profile is determined by detecting the expression level of gene products from at least five genes selected from the group consisting of ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1 using an in vitro assay and wherein the expression level of gene products from the at least five genes is compared with a reference expression level of the at least five genes. In some embodiments, the hypoxia profile is determined by detecting the expression level of gene products from at least ten genes selected from the group consisting of ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1 using an in vitro assay and wherein the expression level of gene products from the at least ten genes is compared with a reference expression level of the at least ten genes. In some embodiments, the hypoxia profile is determined by detecting the expression level of gene products from at least fifteen genes selected from the group consisting of ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1 using an in vitro assay and wherein the expression level of gene products from the at least fifteen genes is compared with a reference expression level of the at least fifteen genes. In some embodiments, the hypoxia profile is determined by detecting the expression level of gene products from at least twenty genes selected from the group consisting of ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1 using an in vitro assay and wherein the expression level of gene products from the at least twenty genes is compared with a reference expression level of the at least twenty genes. In some embodiments, the hypoxia profile is determined by detecting the expression level of gene products from at least twenty-five genes selected from the group consisting of ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1 using an in vitro assay and wherein the expression level of gene products from the at least twenty-five genes is compared with a reference expression level of the at least twenty-five genes. In some embodiments, the hypoxia profile is determined by detecting the expression level of gene products from at least thirty genes selected from the group consisting of ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1 using an in vitro assay and wherein the expression level of gene products from the at least thirty genes is compared with a reference expression level of the at least thirty genes. In some embodiments, the hypoxia profile is determined by detecting the expression level of ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1 using an in vitro assay and wherein the expression level of gene products from the genes is compared with a reference expression level of the at least thirty genes.

In some embodiments, the gene product is a messenger RNA. In some embodiments, the gene product is a protein. In some embodiments, the biological sample is a cervical tumor sample. In some embodiments, the patient has been diagnosed with cervical cancer. In some embodiments, the altered level of expression of the gene products is expressed as a hypoxia score for a tumor. In some embodiments, the hypoxia score is determined by averaging the median centered gene expression levels for the gene products. In some embodiments, a positive hypoxia score is associated with a poor prognosis. In some embodiments, a positive hypoxia score is indicative of a chemoradiotherapy resistance.

In some embodiments, the subject is lymph node negative. In some embodiments, a positive hypoxia score in the subject is indicative of a reduced probability of progression free survival. In some embodiments, a positive hypoxia score is indicative of a chemoradiotherapy resistance.

In some embodiments, the methods further comprise: c) generating a risk profile using the results of steps a) and b).

In some embodiments, the methods further comprise determining a prognosis for the subject, determining a diagnosis for the subject, or selecting the subject for treatment with a particular therapy.

In some embodiments, the present invention provides a set of detection reagents suitable to diagnose or predict cervical cancer comprising reagents for specific detection of gene products from at least one, two, three, five, ten, fifteen, twenty, twenty five, thirty or thirty one genes selected from the group consisting of ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1. In some embodiments, the present invention provides the use of the set of detection reagents for making a diagnostic or prognostic determination of cervical cancer in a subject.

In some embodiments, the present invention provides a kit for detecting the presence of cervical cancer in a mammal, the kit comprising reagents useful, sufficient, or necessary for detecting and/or characterizing the level or presence of gene products from at least one, two, three, five, ten, fifteen, twenty, twenty five, thirty or thirty one genes selected from the group consisting of ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1.

In some embodiments, the present invention provides for the use of hypoxia profile informative reagents for predicting a predisposition to cervical cancer in a subject, diagnosing a cervical cancer in a subject, predicting the likelihood of recurrence of cervical cancer in a subject, providing a prognosis for a subject with cervical cancer, determining the aggressiveness a cervical cancer, or selecting a subject with cervical cancer for treatment with a particular therapy, the reagents comprising one or more reagents for detection of one or more gene product selected from the group consisting of ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1, wherein an altered level of expression of the one or more genes provides an indication selected from the group consisting of an indication of a predisposition of the subject to cervical cancer, an indication that the subject has cervical cancer, an indication of the likelihood of recurrence of the cervical cancer in the subject, an indication of survival of the subject, and indication of the aggressiveness of the cervical cancer, an indication of the likely outcome of treatment of the cervical cancer and an indication that the subject is a candidate for treatment with a particular therapy.

In some embodiments, the reagents comprise one or more reagents for detection of five or more gene products selected from the group consisting of ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1. In some embodiments, the reagents comprise one or more reagents for detection of ten or more gene products selected from the group consisting of ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1. In some embodiments, the reagents comprise one or more reagents for detection of twenty or more gene products selected from the group consisting of ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1. In some embodiments, the reagents comprise one or more reagents for detection of twenty-five or more gene products selected from the group consisting of ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1. In some embodiments, the reagents comprise one or more reagents for detection of ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1.

In some embodiments, the gene product is a messenger RNA. In some embodiments, the gene product is a protein. In some embodiments, the reagents are used to detect gene products in a cervical tumor sample in an in vitro assay. In some embodiments, the subject has been diagnosed with cervical cancer. In some embodiments, the subject is lymph node negative. In some embodiments, the reagents are used to generate a hypoxia score. In some embodiments, the hypoxia score is determined by averaging the median centered gene expression levels for the gene products. In some embodiments, a positive hypoxia score is associated with a poor prognosis. In some embodiments, a positive hypoxia score is indicative of a chemoradiotherapy resistance. In some embodiments, a positive hypoxia score in the subject is indicative of a reduced probability of progression free survival.

Additional embodiments will be apparent to persons skilled in the relevant art based on the teachings contained herein.

DEFINITIONS

Figure 1:
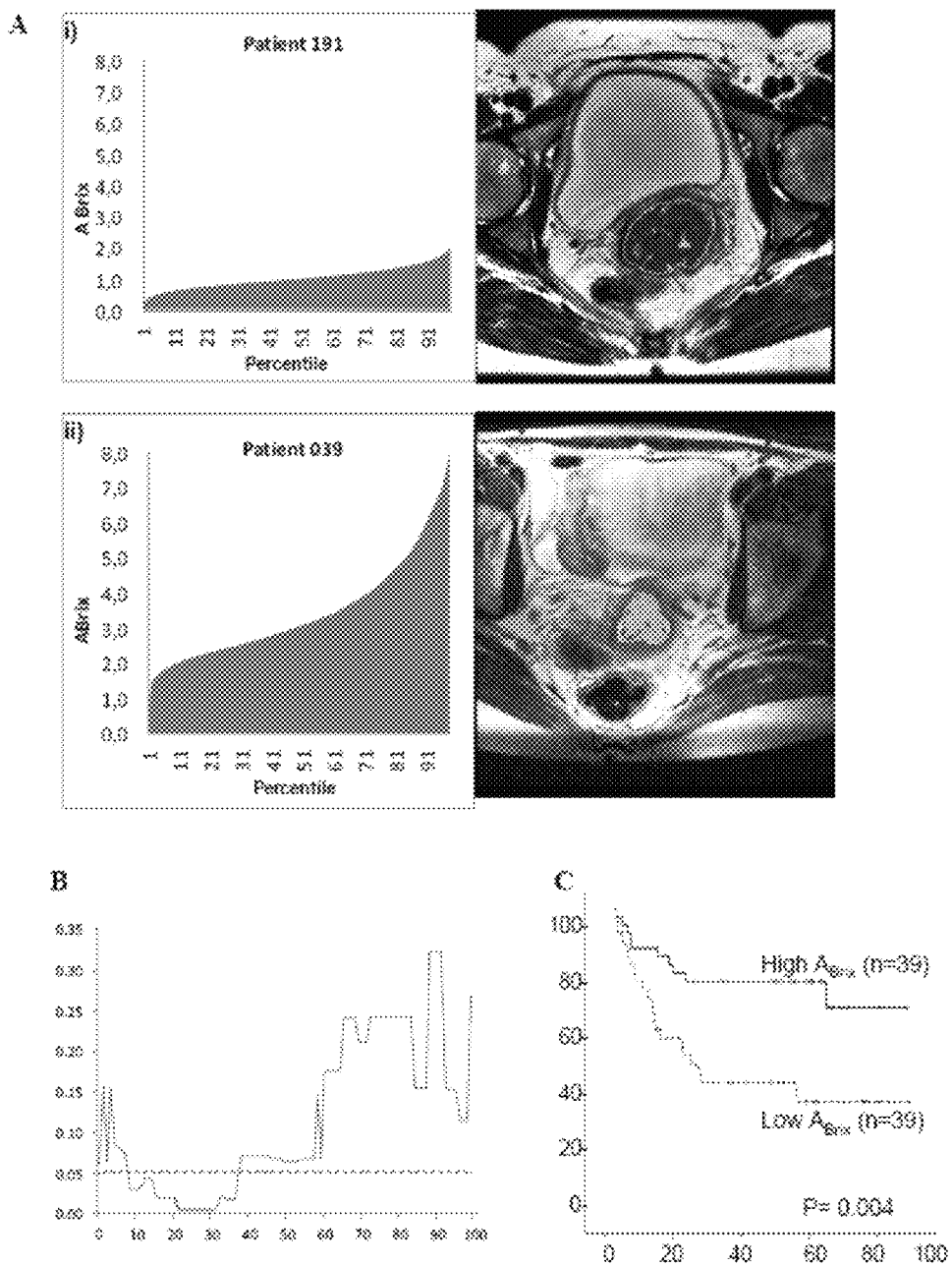
FIGS. 1 A, B and C provide data related to measurement of the ABrix parameter in patients with cervical cancer.

To facilitate an understanding of the present invention, a number of terms and phrases are defined below:

As used herein, the term "sensitivity" is defined as a statistical measure of performance of an assay (e.g., method, test), calculated by dividing the number of true positives by the sum of the true positives and the false negatives.

As used herein, the term "specificity" is defined as a statistical measure of performance of an assay (e.g., method, test), calculated by dividing the number of true negatives by the sum of true negatives and false positives.

As used herein, the term "informative" or "informativeness" refers to a quality of a marker or panel of markers, and specifically to the likelihood of finding a marker (or panel of markers) in a positive sample.

The term "neoplasm" as used herein refers to any new and abnormal growth of tissue. Thus, a neoplasm can be a premalignant neoplasm or a malignant neoplasm. The term "neoplasm-specific marker" refers to any biological material that can be used to indicate the presence of a neoplasm. Examples of biological materials include, without limitation, nucleic acids, polypeptides, carbohydrates, fatty acids, cellular components (e.g., cell membranes and mitochondria), and whole cells.

The term "cervical neoplasm-specific marker" refers to any biological material that can be used to indicate the presence of a cervical neoplasm (e.g., a premalignant cervical neoplasm; a malignant cervical neoplasm). Examples of cervical neoplasm-specific markers include, but are not limited to, ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1.

As used herein, the term "hypoxia profile informative reagent" refers to a reagent or reagents that are informative for identification of expression of a hypoxia profile related to cervical neoplasm. In some embodiments, reagents are primers, probes or antibodies for detection of gene expression products (e.g., RNA transcripts or proteins) of the following genes: ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1.

As used herein, the term "amplicon" refers to a nucleic acid generated using primer pairs. The amplicon is typically single-stranded DNA (e.g., the result of asymmetric amplification), however, it may be RNA or dsDNA.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), hot-start PCR (see, e.g., U.S. Pat. Nos. 5,773,258 and 5,338,671; each herein incorporated by reference in their entireties), intersequence-specfic PCR, inverse PCR (see, e.g., Triglia, et al. (1988) Nucleic Acids Res., 16:8186; herein incorporated by reference in its entirety), ligation-mediated PCR (see, e.g., Guilfoyle, R. et al., Nucleic Acids Research, 25:1854-1858 (1997); U.S. Pat. No. 5,508,169; each of which are herein incorporated by reference in their entireties), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, etl al., (1992) Biotechnology 10:413-417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties).

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced (e.g., in the presence of nucleotides and an inducing agent such as a biocatalyst (e.g., a DNA polymerase or the like) and at a suitable temperature and pH). The primer is typically single stranded for maximum efficiency in amplification, but may alternatively be double stranded. If double stranded, the primer is generally first treated to separate its strands before being used to prepare extension products. In some embodiments, the primer is an oligodeoxyribonucleotide. The primer is sufficiently long to prime the synthesis of extension products in the presence of the inducing agent. The exact lengths of the primers will depend on many factors, including temperature, source of primer and the use of the method. In certain embodiments, the primer is a capture primer.

As used herein, the term "nucleic acid molecule" refers to any nucleic acid containing molecule, including but not limited to, DNA or RNA. The term encompasses sequences that include any of the known base analogs of DNA and RNA including, but not limited to, 4 acetylcytosine, 8-hydroxy-N6-methyladenosine, aziridinylcytosine, pseudoisocytosine, 5-(carboxyhydroxyl-methyl)uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "nucleobase" is synonymous with other terms in use in the art including "nucleotide," "deoxynucleotide," "nucleotide residue," "deoxynucleotide residue," "nucleotide triphosphate (NTP)," or deoxynucleotide triphosphate (dNTP).

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. To further illustrate, oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Typically, the nucleoside monomers are linked by phosphodiester bonds or analogs thereof, including phosphorothioate, phosphorodithioate, phosphoroselenoate, phosphorodiselenoate, phosphoroanilothioate, phosphoranilidate, phosphoramidate, and the like, including associated counterions, e.g., $H^+$, $NH_4^+$, $Na^+$, and the like, if such counterions are present. Further, oligonucleotides are typically single-stranded. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) Meth Enzymol. 68: 90-99; the phosphodiester method of Brown et al. (1979) Meth Enzymol. 68: 109-151; the diethylphosphoramidite method of Beaucage et al. (1981) Tetrahedron Lett. 22: 1859-1862; the triester method of Matteucci et al. (1981) J Am Chem Soc. 103:3185-3191; automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known to those skilled in the art. All of these references are incorporated by reference.

A "sequence" of a biopolymer refers to the order and identity of monomer units (e.g., nucleotides, etc.) in the biopolymer. The sequence (e.g., base sequence) of a nucleic acid is typically read in the 5' to 3' direction.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

The term "gene" refers to a nucleic acid (e.g., DNA) sequence that comprises coding sequences necessary for the production of a polypeptide, RNA (e.g., including but not limited to, mRNA, tRNA and rRNA) or precursor. The polypeptide, RNA, or precursor can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences". Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) processed transcript. The mRNA functions during translation to specify the sequence or order of amino acids in a nascent polypeptide.

The term "locus" as used herein refers to a nucleic acid sequence on a chromosome or on a linkage map and includes the coding sequence as well as 5' and 3' sequences involved in regulation of the gene.

DETAILED DESCRIPTION OF THE INVENTION

The present invention relates to methods and biomarkers for detection of cervical cancer in biological samples, and in particular to markers associated with hypoxia.

Locally advanced cervical cancer is one of the largest groups of malignant diseases that is treated with curative radiotherapy, often combined with cisplatin, as primary treatment. The treatment is challenging, and often associated with severe complications to critical organs within the pelvis due to the high radiation dose needed to ensure locoregional control. MRI is a valuable tool in the handling of cervical cancer, as it is used for staging, treatment planning and response monitoring, where anatomical and morphological features are recorded (2-5). It is a growing interest in the utilization of functional MRI like DCE-MRI to improve disease handling by integrating these features with function. Recently, it has been suggested that DCE-MRI can be used to achieve functional information of the disease, by identifying MRI parameters associated with outcome. This technique may be used to improve diagnosis by selecting patients that are in need for more aggressive treatment. Knowledge of the molecular background of the prognostic images will further open for new possibilities in a clinical setting, by giving information about which additional treatment the patient needs and possibly by pointing to specific molecular targets.

DCE-MRI measures the uptake of a contrast agent in the tumor during a time period and the uptake curves depends on blood perfusion, vascularity and the permeability of the capillaries. The commonly used contrast agent Gd-DTPA (gadopentatate dimeglumine) is perfusion limited, thus the uptake curves will mostly reflect the blood perfusion and the volume of the extracellular, extravascular space. Pharmacokinetic modeling is used to quantitatively describe these biological factors (13). The use of the Brix model (14) is particularly attractive since the arterial input function is not needed, in contrast to the more commonly used Tofts model.

Thus, the present invention clarifies the molecular background of prognostic DCE-MR parameters in cervical cancer patients to identify the underlying reasons for the aggressiveness they are reflecting, in order to improve the usability of DCE-MRI in the clinic. The present inventors first performed unsupervised gene ontology (GO) analysis of genes correlating with ABrix to find biological processes overrepresented in tumors with low levels of this parameter. Based on these results, it was determined that hypoxia and rapid proliferation are important in these tumors, and a supervised gene set analysis applying hypoxia and proliferation related gene sets was performed, together with other gene sets associated with vascularization and aggressiveness. To optimize this analysis, a cervical cancer specific hypoxia gene set was generated from three cervical carcinoma cell lines. This led to the identification of a hypoxia signature which was highly correlated to the DCE-MRI findings and had prognostic impact in an independent cohort of cervical cancer patients.

In some embodiments of the present invention, DCE-MRI and gene expression profiles of patients with cervical cancer are combined. The experimental results demonstrate the usefulness of this approach in detecting a prognostic gene signature. This is the first time it has been shown that the DCE-MRI parameter $A_{Brix}$ is correlated with hypoxia at the molecular level in cancer patients, while simultaneously providing potential novel targets for intervention. These findings demonstrate that DCE-MRI may be used to depict hypoxia, and have important implications for non-invasive detection of treatment resistant tumors and thus candidates for alternative therapy targeting hypoxia.

The GO analysis identified several biological processes significantly correlated to $A_{Brix}$, but did not point to one specific phenotype. The unsupervised gene set analysis, however, clearly identified hypoxia as related to the level of $A_{Brix}$ in the patients. While GO analyses are dependent on genes being annotated to all relevant GOs, gene set analyses allows the utilization of gene sets related to phenotypes based on relevant studies or results from own studies. Response to hypoxia is an example of a GO which is poorly annotated, and therefore might not emerge in a GO analysis although it is important for the data set being analyzed. While the GO analysis in our study did not identify hypoxia as important, it pointed to hypoxia related processes such as metabolism and DNA damage repair, thus supporting the results of the gene set analysis. A study by Hagtvet et al (33) found a correlation between $A_{Brix}$ and hypoxic fraction as determined by pimonidazole. Additionally, hypoxia is known to be associated with radioresistance in cervical cancer (34), which justifies the finding of a relation between this phenotype and the prognostic $A_{Brix}$ parameter.

The present inventors are the first to show that the level of $A_{Brix}$ correlates with hypoxia at the molecular level in cervical cancer patients. In some preferred embodiments, the present invention provides a hypoxia gene profile related to one or more of the following genes: ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1. As shown in more detail in the Examples, thirty-two of the 89 genes up- or downregulated by hypoxia in all three cervical cancer cell lines, including 2 of the genes in the DCE-MRI hypoxia profile, have not previously been shown to be hypoxia-regulated. Even though we have not validated these genes in relation to hypoxia, this finding indicates a need for cervical cancer specific hypoxia response profiles when investigating the importance of hypoxia in cervical tumors.

Of the 31 genes in the DCE-MRI hypoxia profile, eight were known HIF-1α target genes, namely ALDOA, ERO1L, GAPDH, PFKFB4, P4HA2, C4orf3, HMOX1, and STC2. Two of the genes were possibly indirectly coupled with HIF-1α; PYGL has been shown to strongly correlate with VEGF which again is regulated by HIF-1α (35), and RHOC interacts with Von Hippel-Lindau (VHL) (36) which degrades HIF-1α, while one gene is a HIF-2 target gene (SCARB1)(37). Additionally, three of the genes (AK2, DDIT3 (also known as CHOP) and STC2) have been found to be involved in the UPR (38-40), while the remaining genes had unknown functions in hypoxia. It thus appears like processes associated with both HIF-1α, HIF-2, and the UPR may be activated in the hypoxic phenotype depicted by low ABrix. The most important genes for survival in the DCE-MRI hypoxia profile were STC2, DDIT3, and C19orf53. While the functions of C19orf53 are unknown, both STC2 and DDIT3 are interesting genes in regard to hypoxia. STC2 has been associated with poor prognosis in several cancer types (41-43) and has been shown to induce proliferation, inhibit apoptosis and induce invasiveness and epithelial-mesenchymal transition (EMT) in response to HIF-1α or ER stress during hypoxia (40, 44, 45). DDIT3 on the other hand, is a pro-apoptotic protein, which function is to induce G1-S arrest. However, it was recently shown that DDIT3 is involved in the protection of tumor cells during hypoxia through the regulation of autophagy (46), and it was thus proposed that DDIT3 may have a role in influencing the balance between autophagy and apoptosis. Both DDIT3 and STC2 are targets of Activating transcription factor 4 (ATF4), which is induced by eukaryotic translation initiation factor 2-alpha kinase 3 (EIF2AK3/PERK) in response to hypoxic stress. It is contemplated that the combined action these genes in tumors with low $A_{Brix}$ is helping tumor cells adapt to hypoxia by inhibiting apoptosis and inducing autophagy. However, further studies are needed to elucidate the role of these 31 genes in hypoxic cervical tumors with low $A_{brix}$.

The gene sets for proliferation, wound response and radiation response which were analyzed were not specific for cervical cancer. It is possible that results of the analysis regarding these gene sets would have been somewhat different if they had been specific. Combined with the fact that the p-values of both wound healing and proliferation were not very high, we cannot claim that these phenotypes are not related to ABrix.

Using DCE-MRI as a biomarker is advantageous since it is already a routine step in the patient care, in addition to being objective, fast and repeatable. Furthermore, using non-invasive imaging as a surrogate for molecular phenotypes reduces the need of invasive biopsy procedures, and it could also be applied/performed during the course of treatment for response evaluation. Since we identified a list of genes which represents the aggressive hypoxic phenotype visualized by DCE-MRI, the results have therapeutic importance in that they point to possible novel molecular targets in cervical cancer. The results were validated in an independent data set of 109 patients, showing the robustness and usability of the DCE-MRI predicted hypoxia profile. Additionally, we showed that this profile could predict survival of the cervical cancer patients independent on existing clinical markers. Together, the results demonstrate that non-invasive imaging by means of DCE-MRI may be utilized to visualize aggressive hypoxic tumors and thereby identify cervical cancer patients in need of additional or alternative treatment.

Accordingly, in some embodiments, the present invention provides methods for predicting a predisposition to cervical cancer in a subject, diagnosing a cervical cancer in a subject, predicting the likelihood of recurrence of cervical cancer in a subject, providing a prognosis for a subject with cervical cancer, or selecting a subject with cervical cancer for treatment with a particular therapy. In some embodiments, the methods comprise determining or constructing a patient hypoxia profile for a tissue or subsection of tissue from a patient. In some preferred embodiments, the patient hypoxia profile is compared with a reference hypoxia profile. In some embodiments, an altered profile for the patient relative to the reference profile provides an indication selected from the group consisting of an indication of a predisposition of the subject to cervical cancer, an indication that the subject has cervical cancer, an indication of the likelihood of recurrence of the cervical cancer in the subject, an indication of survival of the subject, and indication of the aggressiveness of the cervical cancer, an indication of the likely outcome of treatment of the cervical cancer and an indication that the subject is a candidate for treatment with a particular therapy.

The present invention is not limited to any particular method of generating a hypoxia profile. In some embodiments, the patient hypoxia profile is determined by non-invasive methodology such as magnetic resonance imaging (MRI), DCE-MRI, or PET scan. In some embodiments, the non-invasive procedure utilizes measurement of the $A_{Brix}$ parameter. In other embodiments, the patient hypoxia profile is determined by contacting a biological sample from the patient with reagents for determining a hypoxia profile for the biological sample. In some embodiments, the methods further comprise comparing the hypoxia profile for the biological sample to a reference profile, wherein an altered profile for the sample relative to the reference profile an indication selected from the group consisting of an indication of a predisposition of the subject to cervical cancer, an indication that the subject has cervical cancer, an indication of the likelihood of recurrence of the cervical cancer in the subject, an indication of survival of the subject, and indication of the aggressiveness of the cervical cancer, an indication of the likely outcome of treatment of the cervical cancer and an indication that the subject is a candidate for treatment with a particular therapy. In some embodiments, the reagents are specific for the detection of one or more gene products (e.g., RNA or proteins) resulting from the expression of one or more of the following genes: ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1.

While the present invention exemplifies several markers specific for detecting cervical cancer, any marker that is correlated with the presence or absence of cervical cancer may be used in conjunction with the identified markers. A marker, as used herein, includes, for example, nucleic acid(s) whose production or mutation or lack of production is characteristic of a cervical neoplasm. Depending on the particular set of markers employed in a given analysis, the statistical analysis will vary. For example, where a particular combination of markers is highly specific for cervical cancer, the statistical significance of a positive result will be high. It may be, however, that such specificity is achieved at the cost of sensitivity (e.g., a negative result may occur even in the presence of cervical cancer). By the same token, a different combination may be very sensitive (e.g., few false negatives, but has a lower specificity).

Particular combinations of markers may be used that show optimal function with different ethnic groups or sex, different geographic distributions, different stages of disease, different degrees of specificity or different degrees of sensitivity. Particular combinations may also be developed which are particularly sensitive to the effect of therapeutic regimens on disease progression. Subjects may be monitored after a therapy and/or course of action to determine the effectiveness of that specific therapy and/or course of action.

The methods of the present invention are not limited to particular indicators of cervical neoplasm.

As described above, embodiments of the present invention provide diagnostic and screening methods that utilize the detection of gene products resulting from the expression of one or more of the following genes: ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1. Exemplary, non-limiting methods are described below.

Any patient sample may be tested according to methods of embodiments of the present invention. By way of non-limiting examples, the sample may be a tissue sample (e.g., a cervical tumor biopsy sample or pelvic lymph node biopsy).

In some embodiments, the patient sample is subjected to preliminary processing designed to isolate or enrich the sample for the gene products or cells that contain the gene products. A variety of techniques known to those of ordinary skill in the art may be used for this purpose, including but not limited to: centrifugation; immunocapture; cell lysis; and, nucleic acid target capture (See, e.g., EP Pat. No. 1 409 727, herein incorporated by reference in its entirety).

Particular combinations of markers may be used that show optimal function with different ethnic groups or sex, different geographic distributions, different stages of disease, different degrees of specificity or different degrees of sensitivity. Particular combinations may also be developed which are particularly sensitive to the effect of therapeutic regimens on disease progression. Subjects may be monitored after a therapy and/or course of action to determine the effectiveness of that specific therapy and/or course of action. Markers for other cancers, diseases, infections, and metabolic conditions are also contemplated for inclusion in a multiplex or panel format.

I. DNA and RNA Detection—Hypoxia Profile Informative Reagents

The gene products of the present invention are detected using a variety of nucleic acid techniques known to those of ordinary skill in the art, including but not limited to: nucleic acid sequencing; nucleic acid hybridization; and, nucleic acid amplification. In particular, the gene products are detected with hypoxia profile informative reagents specific for the gene products of one or more of the following genes: ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1. Thus the hypoxia profile informative reagents may comprise reagents such as primers and probes for detection of the gene products by sequencing, hybridization, amplification, microarray analysis, and related methodologies.

1. Sequencing

Illustrative non-limiting examples of nucleic acid sequencing techniques include, but are not limited to, chain terminator (Sanger) sequencing and dye terminator sequencing. Those of ordinary skill in the art will recognize that because RNA is less stable in the cell and more prone to nuclease attack experimentally RNA is usually reverse transcribed to DNA before sequencing.

Chain terminator sequencing uses sequence-specific termination of a DNA synthesis reaction using modified nucleotide substrates. Extension is initiated at a specific site on the template DNA by using a short radioactive, or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

A variety of nucleic acid sequencing methods are contemplated for use in the methods of the present disclosure including, for example, chain terminator (Sanger) sequencing, dye terminator sequencing, and high-throughput sequencing methods. Many of these sequencing methods are well known in the art. See, e.g., Sanger et al., Proc. Natl. Acad. Sci. USA 74:5463-5467 (1997); Maxam et al., Proc. Natl. Acad. Sci. USA 74:560-564 (1977); Drmanac, et al., Nat. Biotechnol. 16:54-58 (1998); Kato, Int. J. Clin. Exp. Med. 2:193-202 (2009); Ronaghi et al., Anal. Biochem. 242:84-89 (1996); Margulies et al., Nature 437:376-380 (2005); Ruparel et al., Proc. Natl. Acad. Sci. USA 102:5932-5937 (2005), and Harris et al., Science 320:106-109 (2008); Levene et al., Science 299:682-686 (2003); Korlach et al., Proc. Natl. Acad. Sci. USA 105:1176-1181 (2008); Branton et al., Nat. Biotechnol. 26(10):1146-53 (2008); Eid et al., Science 323:133-138 (2009); each of which is herein incorporated by reference in its entirety.

A number of DNA sequencing techniques are known in the art, including fluorescence-based sequencing methodologies (See, e.g., Birren et al., Genome Analysis: Analyzing DNA, 1, Cold Spring Harbor, N.Y.; herein incorporated by reference in its entirety). In some embodiments, automated sequencing techniques understood in that art are utilized. In some embodiments, parallel sequencing of partitioned amplicons (PCT Publication No: WO2006084132 to Kevin McKernan et al., herein incorporated by reference in its entirety) is utilized. In some embodiments, bridge amplification (see, e.g., WO 2000/018957, U.S. Pat. Nos. 7,972,820; 7,790,418 and Adessi et al., Nucleic Acids Research (2000): 28(20): E87; each of which are herein incorporated by reference) is utilized. In some embodiments, DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties) is utilized. Additional examples of sequencing techniques include the Church polony technology (Mitra et al., 2003, Analytical Biochemistry 320, 55-65; Shendure et al., 2005 Science 309, 1728-1732; U.S. Pat. No. 6,432,360, U.S. Pat. No. 6,485,944, U.S. Pat. No. 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. No. 6,787,308; U.S. Pat. No. 6,833,246; herein incorporated by reference in their entireties), the Lynx massively parallel signature sequencing technology (Brenner et al. (2000). Nat. Biotechnol. 18:630-634; U.S. Pat. No. 5,695,934; U.S. Pat. No. 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., Clinical Chem., 55: 641-658, 2009; MacLean et al., Nature Rev. Microbiol., 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., Life Technologies/Ion Torrent, and Pacific Biosciences, respectively.

2. Hybridization

Illustrative non-limiting examples of nucleic acid hybridization techniques include, but are not limited to, in situ hybridization (ISH), microarray, and Southern or Northern blot. In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts (e.g., gene products) within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

In some embodiments, gene products are detected using fluorescence in situ hybridization (FISH). In some embodiments, FISH assays utilize bacterial artificial chromosomes (BACs). These have been used extensively in the human genome sequencing project (see *Nature* 409: 953-958 (2001)) and clones containing specific BACs are available through distributors that can be located through many sources, e.g., NCBI. Each BAC clone from the human genome has been given a reference name that unambiguously identifies it. These names can be used to find a corresponding GenBank sequence and to order copies of the clone from a distributor. Specific protocols are well known in the art and can be readily adapted for the present invention. Guidance regarding methodology may be obtained from many references including: *In situ Hybridization: Medical Applications* (eds. G. R. Coulton and J. de Belleroche), Kluwer Academic Publishers, Boston (1992); *In situ Hybridization: In Neurobiology; Advances in Methodology* (eds. J. H. Eberwine, K. L. Valentino, and J. D. Barchas), Oxford University Press Inc., England (1994); *In situ Hybridization: A Practical Approach* (ed. D. G. Wilkinson), Oxford University Press Inc., England (1992)); Kuo, et al., *Am. J. Hum. Genet.* 49:112-119 (1991); Klinger, et al., *Am. J. Hum. Genet.* 51:55-65 (1992); and Ward, et al., *Am. J. Hum. Genet.* 52:854-865 (1993)). There are also kits that are commercially available and that provide protocols for performing FISH assays (available from e.g., Oncor, Inc., Gaithersburg, Md.). Patents providing guidance on methodology include U.S. Pat. Nos. 5,225,326; 5,545,524; 6,121,489 and 6,573,043. All of these references are hereby incorporated by reference in their entirety and may be used along with similar references in the art and with the information provided in the Examples section herein to establish procedural steps convenient for a particular laboratory.

In some embodiments, the present invention utilizes nuclease protection assays. Nuclease protection assays are useful for identification of one or more RNA molecules of known sequence even at low total concentration. The extracted RNA is first mixed with antisense RNA or DNA probes that are complementary to the sequence or sequences of interest and the complementary strands are hybridized to form double-stranded RNA (or a DNA-RNA hybrid). The mixture is then exposed to ribonucleases that specifically cleave only single-stranded RNA but have no activity against double-stranded RNA. When the reaction runs to completion, susceptible RNA regions are degraded to very short oligomers or to individual nucleotides; the surviving RNA fragments are those that were complementary to the added antisense strand and thus contained the sequence of interest. Suitable nuclease protection assays, include, but are not limited to those described in U.S. Pat. No. 5,770,370; EP 2290101A3; US 20080076121; US 20110104693; each of which is incorporated herein by reference in its entirety. In some embodiments, the present invention utilizes the quantitative nuclease protection assay provided by HTG Molecular Diagnostics, Inc. (Tuscon, Ariz.).

3. Microarrays

Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes or transcripts (e.g., gene products) by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

In some embodiments, the present invention utilizes digital molecular barcoding technology, preferably in conjunction with an nCounter Analysis System (Nanostring Technologies, Seattle, Wash.) for the detection of gene expression products. This technique utilizes a digital color-coded barcode technology that is based on direct multiplexed measurement of gene expression and offers high levels of precision and sensitivity (>1 copy per cell). The technology uses molecular "barcodes" and single molecule imaging to detect and count hundreds of unique transcripts in a single reaction. Each color-coded barcode is attached to a single target-specific probe corresponding to a gene of interest. Mixed together with controls, they form a multiplexed CodeSet. Each color-coded barcode represents a single target molecule. Barcodes hybridize directly to the target molecules and can be individually counted. In preferred embodiments, a hybridization step employs two ~50 base probes (the capture and reporter probes) per mRNA that hybridize in solution. The reporter probe carries the barcode signal; the capture probe allows the complex to be immobilized for data collection. After hybridization, the excess probes are removed and the probe/target complexes aligned and immobilized in an nCounter Cartridge. Sample cartridges are placed in a digital analyzer for data collection. Color codes on the surface of the cartridge are counted and tabulated for each target molecule. See e.g., U.S. Pat. Publ. 20100015607, 20100047924; and 20100112710; each of which is incorporated by reference herein in its entirety.

4. Amplification

Nucleic acids (e.g., gene products) may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800,159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399, 491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *BioTechnol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

In some embodiments, the present invention utilizes multiplexed amplification and detection techniques. See, e.g., Wong et al., *Biotechniques* (2005) 39(1):1-11; and Bustin, J. Mol. Endocrinol. (2000) 25: 169-193; each of which is incorporated by reference herein in its entirety. Suitable multiplexed amplification-based detection techniques include, but are not limited to, the hybridization probe four oligonucleotide method, the hybridization probe three oligonucleotide method, and methods utilizing hydrolysis probes (two primers and one specific probe per target molecule), molecular beacons (two primers and one specific probe per target molecule), scorpions, sunrise primers (two PCR primers per target molecule), and LUX primers (two PCR primer per target molecule). Another suitable multiplexed, amplification-based technique is the ICEP1ex/STAR technology system from PrimeraDX (Mansfield, Mass.). This technique utilizes end-labeled PCR for amplification of specific target molecules followed by detection by real time sampling via capillary electrophoresis. See e.g., U.S. Pat. Publ. 20100221725; 20110300537; and 20120100600; each of which is incorporated by reference herein in its entirety.

5. Detection Methods

Non-amplified or amplified nucleic acids can be detected by any conventional means. For example, the gene products can be detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541,205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, herein incorporated by reference in its entirety.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed in U.S. Pat. Nos. 5,925,517 and 6,150,097, herein incorporated by reference in its entirety.

Other self-hybridizing probes are well known to those of ordinary skill in the art. By way of non-limiting example, probe binding pairs having interacting labels, such as those disclosed in U.S. Pat. No. 5,928,862 (herein incorporated by reference in its entirety) might be adapted for use in the present invention. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products in the present invention. See, e.g., U.S. Pat. No. 5,814,447 (herein incorporated by reference in its entirety).

II. Protein Detection—Hypoxia Profile Informative Reagents

The gene products of the present invention may further be proteins and be detected using a variety of protein detection techniques known to those of ordinary skill in the art, including but not limited to: sequencing, mass spectrometry and immunoassays. In particular, the gene products are detected with hypoxia profile informative reagents specific for the protein gene products of one or more of the following genes: ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1. Thus the hypoxia profile informative reagents may comprise reagents such as antibodies (e.g., primary and secondary antibodies) and other protein detection probes.

1. Sequencing

Illustrative non-limiting examples of protein sequencing techniques include, but are not limited to, mass spectrometry and Edman degradation.

Mass spectrometry can, in principle, sequence any size protein but becomes computationally more difficult as size increases. A protein is digested by an endoprotease, and the resulting solution is passed through a high pressure liquid chromatography column. At the end of this column, the solution is sprayed out of a narrow nozzle charged to a high positive potential into the mass spectrometer. The charge on the droplets causes them to fragment until only single ions remain. The peptides are then fragmented and the mass-charge ratios of the fragments measured. The mass spectrum is analyzed by computer and often compared against a database of previously sequenced proteins in order to determine the sequences of the fragments. The process is then repeated with a different digestion enzyme, and the overlaps in sequences are used to construct a sequence for the protein.

In the Edman degradation reaction, the peptide to be sequenced is adsorbed onto a solid surface (e.g., a glass fiber coated with polybrene). The Edman reagent, phenylisothiocyanate (PTC), is added to the adsorbed peptide, together with a mildly basic buffer solution of 12% trimethylamine, and reacts with the amine group of the N-terminal amino acid. The terminal amino acid derivative can then be selectively detached by the addition of anhydrous acid. The derivative isomerizes to give a substituted phenylthiohydantoin, which can be washed off and identified by chromatography, and the cycle can be repeated. The efficiency of each step is about 98%, which allows about 50 amino acids to be reliably determined 2. Immunoassays Illustrative non-limiting examples of immunoassays include, but are not limited to: immunoprecipitation; Western blot; ELISA; immunohistochemistry; immunocytochemistry; flow cytometry; and, immuno-PCR. Polyclonal or monoclonal antibodies detectably labeled using various techniques known to those of ordinary skill in the art (e.g., colorimetric, fluorescent, chemiluminescent or radioactive) are suitable for use in the immunoassays.

Immunoprecipitation is the technique of precipitating an antigen out of solution using an antibody specific to that antigen. The process can be used to identify protein complexes present in cell extracts by targeting a protein believed to be in the complex. The complexes are brought out of solution by insoluble antibody-binding proteins isolated initially from bacteria, such as Protein A and Protein G. The antibodies can also be coupled to sepharose beads that can easily be isolated out of solution. After washing, the precipitate can be analyzed using mass spectrometry, Western blotting, or any number of other methods for identifying constituents in the complex.

A Western blot, or immunoblot, is a method to detect protein in a given sample of tissue homogenate or extract. It uses gel electrophoresis to separate denatured proteins by mass. The proteins are then transferred out of the gel and onto a membrane, typically polyvinyldiflroride or nitrocellulose, where they are probed using antibodies specific to the protein of interest. As a result, researchers can examine the amount of protein in a given sample and compare levels between several groups.

An ELISA, short for Enzyme-Linked ImmunoSorbent Assay, is a biochemical technique to detect the presence of an antibody or an antigen in a sample. It utilizes a minimum of two antibodies, one of which is specific to the antigen and the other of which is coupled to an enzyme. The second antibody will cause a chromogenic or fluorogenic substrate to produce a signal. Variations of ELISA include sandwich ELISA, competitive ELISA, and ELISPOT. Because the ELISA can be performed to evaluate either the presence of antigen or the presence of antibody in a sample, it is a useful tool both for determining serum antibody concentrations and also for detecting the presence of antigen.

Immunohistochemistry and immunocytochemistry refer to the process of localizing proteins in a tissue section or cell, respectively, via the principle of antigens in tissue or cells binding to their respective antibodies. Visualization is enabled by tagging the antibody with color producing or fluorescent tags. Typical examples of color tags include, but are not limited to, horseradish peroxidase and alkaline phosphatase. Typical examples of fluorophore tags include, but are not limited to, fluorescein isothiocyanate (FITC) or phycoerythrin (PE).

Flow cytometry is a technique for counting, examining and sorting microscopic particles suspended in a stream of fluid. It allows simultaneous multiparametric analysis of the physical and/or chemical characteristics of single cells flowing through an optical/electronic detection apparatus. A beam of light (e.g., a laser) of a single frequency or color is directed onto a hydrodynamically focused stream of fluid. A number of detectors are aimed at the point where the stream passes through the light beam; one in line with the light beam (Forward Scatter or FSC) and several perpendicular to it (Side Scatter (SSC) and one or more fluorescent detectors). Each suspended particle passing through the beam scatters the light in some way, and fluorescent chemicals in the particle may be excited into emitting light at a lower frequency than the light source. The combination of scattered and fluorescent light is picked up by the detectors, and by analyzing fluctuations in brightness at each detector, one for each fluorescent emission peak, it is possible to deduce various facts about the physical and chemical structure of each individual particle. FSC correlates with the cell volume and SSC correlates with the density or inner complexity of the particle (e.g., shape of the nucleus, the amount and type of cytoplasmic granules or the membrane roughness).

Immuno-polymerase chain reaction (IPCR) utilizes nucleic acid amplification techniques to increase signal generation in antibody-based immunoassays. Because no protein equivalence of PCR exists, that is, proteins cannot be replicated in the same manner that nucleic acid is replicated during PCR, the only way to increase detection sensitivity is by signal amplification. The target proteins are bound to antibodies which are directly or indirectly conjugated to oligonucleotides. Unbound antibodies are washed away and the remaining bound antibodies have their oligonucleotides amplified. Protein detection occurs via detection of amplified oligonucleotides using standard nucleic acid detection methods, including real-time methods.

In some embodiments, mass spectrometry is utilized to detect protein gene expression products. Preferred techniques include, but are not limited to, matrix-assisted laser desorption/ionization time of flight (MALDI-TOF MS) and electrospray mass spectrometry (ESMS). See, e.g., Mann et al., Annu. Rev. Biochem (2001) 70:437-73.

III. Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., presence or absence of a pseudogene) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease or as a companion diagnostic to determine a treatment course of action.

IV. In Vivo Imaging

Gene products may also be detected using in vivo imaging techniques, including but not limited to: radionuclide imaging; positron emission tomography (PET); computerized axial tomography, X-ray or magnetic resonance imaging method, fluorescence detection, and chemiluminescent detection. In some embodiments, in vivo imaging techniques are used to visualize the presence of or expression of cancer markers in an animal (e.g., a human or non-human mammal). For example, in some embodiments, cancer marker mRNA or protein is labeled using a labeled antibody specific for the cancer marker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the cancer markers of the present invention are described below.

The in vivo imaging methods of embodiments of the present invention are useful in the identification of cancers that express gene products (e.g., cervical cancer). In vivo imaging is used to visualize the presence or level of expression of a ncRNA. Such techniques allow for diagnosis without the use of an unpleasant biopsy. The in vivo imaging methods of embodiments of the present invention can further be used to detect metastatic cancers in other parts of the body.

In some embodiments, reagents (e.g., antibodies) specific for the cancer markers of the present invention are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107, herein incorporated by reference).

In other embodiments, antibodies are radioactively labeled. The use of antibodies for in vivo diagnosis is well known in the art. Sumerdon et al., (Nucl. Med. Biol 17:247-254 [1990] have described an optimized antibody-chelator for the radioimmunoscintographic imaging of tumors using Indium-111 as the label. Griffin et al., (J Clin One 9:631-640 [1991]) have described the use of this agent in detecting tumors in patients suspected of having recurrent colorectal cancer. The use of similar agents with paramagnetic ions as labels for magnetic resonance imaging is known in the art (Lauffer, Magnetic Resonance in Medicine 22:339-342 [1991]). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetiium-99m (6 hours), and indium-111 (3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 [1980]) for In-111 and Tc-99m, and by Scheinberg et al. (Science 215:1511 [1982]). Other chelating agents may also be used, but the 1-(p-carboxymethoxybenzyl)EDTA and the carboxy-carbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 [1982]) for labeling of albumin with In-111, but which can be adapted for labeling of antibodies. A suitable method of labeling antibodies with Tc-99m which does not use chelation with DPTA is the pretinning method of Crockford et al., (U.S. Pat. No. 4,323,546, herein incorporated by reference).

A method of labeling immunoglobulins with Tc-99m is that described by Wong et al. (Int. J. Appl. Radiat. Isot., 29:251 [1978]) for plasma protein, and recently applied successfully by Wong et al. (J. Nucl. Med., 23:229 [1981]) for labeling antibodies.

In the case of the radiometals conjugated to the specific antibody, it is likewise desirable to introduce as high a proportion of the radiolabel as possible into the antibody molecule without destroying its immunospecificity. A further improvement may be achieved by effecting radiolabeling in the presence of the ncRNA, to insure that the antigen binding site on the antibody will be protected. The antigen is separated after labeling.

In still further embodiments, in vivo biophotonic imaging (Xenogen, Almeda, Calif.) is utilized for in vivo imaging. This real-time in vivo imaging utilizes luciferase. The luciferase gene is incorporated into cells, microorganisms, and animals (e.g., as a fusion protein with a cancer marker of the present invention). When active, it leads to a reaction that emits light. A CCD camera and software is used to capture the image and analyze it.

V. Compositions & Kits

Compositions for use in the diagnostic methods described herein include, but are not limited to, kits comprising one or more hypoxia profile informative reagents as described above. In some embodiments, the kits comprise one or more hypoxia profile informative reagents for detecting altered gene expression in a sample from a subject having or suspected of having cervical cancer, wherein the reagents are specific detection of one or more gene products from the following genes: ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1.

In some embodiments, the kits contain hypoxia profile informative reagents specific for a cancer gene marker, in addition to detection reagents and buffers. In preferred embodiments, the hypoxia profile informative reagent is a probe(s) that specifically hybridizes to a respective gene product(s) of the one or more genes, a set(s) of primers that amplify a respective gene product(s) of the one or more genes, an antigen binding protein(s) that binds to a respective gene product(s) of the one or more genes, or a sequencing primer(s) that hybridizes to and allows sequencing of a respective gene product(s) of the one or more genes. The probe and antibody compositions of the present invention may also be provided in the form of an array. In preferred embodiments, the kits contain all of the components necessary to perform a detection assay, including all controls, directions for performing assays, and any necessary software for analysis and presentation of results.

In some embodiments, the kits include instructions for using the reagents contained in the kit for the detection and characterization of cancer in a sample from a subject. In some embodiments, the instructions further comprise the statement of intended use required by the U.S. Food and Drug Administration (FDA) in labeling in vitro diagnostic products. The FDA classifies in vitro diagnostics as medical devices and requires that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use. Where applicable, photographs or engineering drawings should be supplied; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; 8) Any additional information regarding the in vitro diagnostic product requested that is necessary for the FDA to make a substantial equivalency determination. Additional information is available at the Internet web page of the U.S. FDA.

VI. Methods of Use

As disclosed herein, the present invention provides hypoxia informative reagents and methods for determining a prognosis of cervical cancer in a subject, diagnosing a cervical cancer in a subject, predicting a predisposition to cervical cancer in a subject, predicting the likelihood of recurrence of cervical cancer in a subject, assessing the aggressiveness of a cervical cancer in a subject, or selecting a subject with a disease for treatment with a particular therapy. In some preferred embodiments, embodiments of the present invention provide compositions and methods for providing a prognosis to a patient diagnosed with cervical cancer. For example, in some embodiments, altered gene expression of one or more of the hypoxia profile genes (e.g., ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and/or TRAPPC1) relative to a control sample (e.g., non-cancerous cervical tissue or a reference cervical tumor sample) is associated with a poor prognosis. In some embodiments, the altered expression is an increase in expression of one or more of the hypoxia profile genes identified above. In some embodiments, the reference level is from a cervical cancer tumor. In some embodiments, the reference level is cancer free cervical tissue. In some embodiments, the level of expression as compared to the reference level is indicative of a poor prognosis. In some embodiments, the poor prognosis is a decreased chance of survival. In some embodiments, the poor prognosis is an increased chance of recurrence or metastasis of cervical cancer. In some embodiments, the prognosis is the likelihood of 5 year relapse free survival.

In some embodiments, the expression levels of one or more of the hypoxia profile genes are determined and used to generate a hypoxia score. In some embodiments, the hypoxia score is determined by averaging the median centered gene expression levels (preferably converted to logarithmic scale) for one or more of the hypoxia profile genes (e.g., 1 or more, five or, ten or more, 20 or more, twenty-five or more, or the entire set of thirty-one genes). A positive hypoxia score (i.e., increased expression of the hypoxia profile genes) is associated with a poor prognosis. In some embodiments, a positive hypoxia score (or increased expression of the hypoxia profile genes) is indicative of a chemo-radiotherapy resistance. In some embodiments, a positive hypoxia score (or increased expression of the hypoxia profile genes) for the sample is indicative of a reduced probability of progression free survival in the subject.

In some embodiments, the assays and detection methods of the present invention are used to stratify patients into subgroups. In some embodiments, the subjects are either lymph node positive or lymph node negative. In lymph node negative patients, a positive hypoxia score (i.e., increased expression of the hypoxia profile genes) is associated with a poor prognosis. In some embodiments, a positive hypoxia score (or increased expression of the hypoxia profile genes) in a lymph node negative subject is indicative of a chemo-radiotherapy resistance. In some embodiments, a positive hypoxia score (or increased expression of the hypoxia profile genes) for the sample from a lymph node negative subject is indicative of a reduced probability of progression free survival in the subject.

In some embodiments, the prognostic information is used to determine a treatment course of action for the subject. For example, in some embodiments, subjects found to have a poor prognosis can be given a therapy in addition to chemo-radiotherapy. In further embodiments, the assays of the present invention are utilized during clinical testing of therapeutic agents for cervical cancer. It is contemplated that the assays for gene products as described above will define specific patient populations for which treatment with the therapeutic agent is more or less effective than the patient population as a whole. Thus, in some embodiments of the present invention, methods are provided where subjects are screened using the assays of the present invention and patients with a particular profile of gene expression as described above are selected for treatment with a particular therapeutic agent or therapeutic regime.

VII. Drug Screening Applications

In some embodiments, the present invention provides drug screening assays (e.g., to screen for anticancer drugs). The screening methods of the present invention utilize the gene products described above. For example, in some embodiments, the present invention provides methods of screening for compounds that alter (e.g., decrease) the expression or activity of gene products. The compounds or agents may interfere with transcription, by interacting, for example, with the promoter region. The compounds or agents may interfere with mRNA (e.g., by RNA interference, antisense technologies, etc.). The compounds or agents may interfere with pathways that are upstream or downstream of the biological activity of gene products. In some embodiments, candidate compounds are antisense or interfering RNA agents (e.g., oligonucleotides) directed against gene products. In other embodiments, candidate compounds are antibodies or small molecules that specifically bind to a gene products regulator or expression products inhibit its biological function.

EXAMPLES

The following examples are provided in order to demonstrate and further illustrate certain preferred embodiments and aspects of the present invention and are not to be construed as limiting the scope thereof.

Example 1

Materials and Methods

Patients and Tumor Specimens

A total of 190 patients with carcinoma of the uterine cervix, prospectively recruited to our chemoradiotherapy protocol at the Norwegian Radium Hospital were included (supplementary table 1), all treated with external irradiation and brachytherapy combined with adjuvant cisplatin and followed up as described previously (22). From the 81 patients on which DCE-MRI were performed, three patients were excluded because the pharmacokinetic models could not successfully be fitted to the contrast uptake curves of the tumor, resulting in a total of 78 patients in the current study. Pathological lymph nodes in the pelvis at the time of diagnosis were detected by magnetic resonance imaging or, in a few cases, computed tomography. A lymph node was classified as pathological whenever the short axis was equal to or exceeded 10 mm, according to the response evaluation criteria in solid tumors (RECIST) version 1.1 (23). The time between diagnosis and the first event of relapse or cancer related death was recorded. Relapse (progressive disease) was classified as locoregional (regression within the irradiated field), distant, or both. 13 patients died of causes not related to cancer and were censored.

Tumor specimens were taken before the start of therapy, fixed in 4% buffered formalin, paraffin-embedded, and used for immunohistochemistry. Separate biopsies for each tumor were snap frozen, stored at −80 C, and used for Western blotting and gene expression analysis. The study was approved by the regional committee of medical research ethics in southern Norway, and written informed-consent was achieved from all patients.

SUPPLEMENTARY TABLE 1

| Characteristic | DCE-MRI patients/cohort | | Validation patients/cohort | |
|---|---|---|---|---|
| | No | % | No | % |
| Diagnostic | | | | |
| No. of patients | 78 | | 109 | |
| Age (years) | | | | |
| Median | 56.5 | | 55.0 | |
| Range | 31.6-83.1 | | 23.8-84.2 | |
| FIGO stage | | | | |
| 1B | 2 | 3 | 9 | 8 |
| 2 | 41 | 53 | 74 | 68 |
| 3 | 29 | 37 | 20 | 18 |
| 4 | 6 | 8 | 6 | 6 |
| Tumor volume (cm$^2$) | | | | |
| Median | 45.6 | | 39.3 | |
| Range | 2.8-321.0 | | 1.9-302.4 | |
| Pelvic lymph node | | | | |
| Positive | 31 | 40 | 45 | 41 |
| Negative | 47 | 60 | 64 | 59 |
| Follow up data | | | | |
| Observation time | | | | |
| Median | 60.9 | | 30.4 | |
| Range | 17.7-100.0 | | 5.5-104.0 | |
| Relapse | | | | |
| Locoregional only | | | | |
| Distant only | | | | |
| Locoregional and | | | | |
| Cancer related | | | | |

DCE-MRI Dynamic Contrast Enhanced Magnetic Resonance Imaging; FIGO, Federation International de Gynecologic et d'Obstetrique
*Determined from pre-treatment magnetic resonance images and calculated based on 3 orthogonal diameters (a, b, c) as (π/6) abc.
†Based on patients without distant or locoregional relapse DCE-MRI of Cervical Cancer Patients For 78 patients, MRI measurements were performed on a 1.5 T Signa Horizon LX tomography (GE Medical Systems, Milwaukee, Wis.). Prior to treatment, all patients underwent DCE-MRI in addition to T2-weighted imaging. For delineation of the tumor, axial T2-weighted fast spin echo image series were included in the imaging protocol. To record the DCE-MRI series, an axial T1-weighted fast spoiled gradient recalled (FSPGR) sequence was utilized, including the entire tumor volume in the field of view. A fast bolus injection with a dose of 0.1 mmol/kg body weight of Gd-DTPA (Magnevist®; Schering, Berlin, Germany) was used. The sequence of DCE-MRI included 14 image series during a time period of 5 minutes, of which one series was recorded before the bolus injection and 13 after. The temporal resolution differed between 15 s (early time points) and 1 min (late time points).

Image Analysis/Pharmacokinetic Analysis

The relative signal increase (RSI) for each patient was calculated for each tumor voxel and time point:

(1) Where $S(t)$ is the signal intensity at time t. The precontrast images obtained at $t=0$ were used as baseline, so that RSI describes the time dependence of the relative concentration after tracer injection. Using Levenberg-Marquardt least squares minimization (24), the Brix model (25) was fitted to the RSI in each tumor voxel, using the relation:

(2) where ABrix is the amplitude, kep the transfer rate of tracer from tissue to plasma, and kel the clearance rate of the tracer from plasma. All three parameters were allowed to vary freely in the fitting, except for the constraints ABrix, kep, kel≥0.5

Cell Lines and Hypoxia Treatment

The HeLa, SiHa and CaSki cervix cancer cell lines were used as an in vitro model of hypoxia. The cells were incubated in Dulbecco's Modified Eagle medium with GlutaMAX containing 10% fetal calf serum (FCS) and penicillin streptomycin under a 5% $CO_2$ atmosphere at 37° C., and subcultured twice a week. 50-80% confluent cells were maintained in this medium under hypoxic (0.2% O2, 5% CO2) or normoxic (95% air, 5% Co2) conditions for 24 h at 37° C. Hypoxic treatment was performed in an Invivo2200 chamber (Ruskinn Technology Ltd, Bridgend, UK) with accurate O2 and CO2 controls. The treatment conditions of 24 h with 0.2% O2 was selected to reflect conditions with prolonged hypoxia and to ensure a response by HIF-1α and possibly by the unfolded protein response (UPR) (26, 27).

Flow cytometry was performed to investigate whether hypoxia treatment caused changes in the cell cycle distribution or induced apoptosis in the cell lines. (Supplementary figure). Western blots were performed by lysing cells with 10 mM Tris HCl pH 7.5 lysis buffer containing 2% SDS, and Na3vO4, separating the proteins by 8% Tris-HEPES-SDS polyacrylamide gels (Pierce Biotechnology, Rockford, Ill.), and further blotting them on a PVDF membrane where they were and stained with antibodies against HIF-1α and secondary antibody LumiGLO Chemiluminescent substrate system (KPL, Gaithersburg, Md.) was used for detection.

Gene Expression Analysis

Gene expression profiling 122 patients as well as the three cell lines was performed, using the Illumina beadarrays human WG6v3 (Illumina Inc., San Diego, Calif.) with 48803 transcripts, as described (28). In brief, total RNA was isolated from the frozen specimens by using Trizol reagent (Invitrogen, Carlsbad, Calif.) (29) and from the cell lines using RNeasy MiniKit (Quiagen), according to the manufacturers' instructions. The quality of the RNA samples was confirmed using the Agilent 2100 Bioanalyzer (Agilent Technologies, Santa Clara, Calif. The Illumina® TotalPrep RNA amplification kit (Ambion Inc., Austin, Tex.) was used to amplify RNA, using 500 ng of total RNA as input material. cRNA was synthesized overnight, labeled, and hybridized to the arrays at 58° C. overnight. The hybridized arrays were stained with streptavidin-Cy3 (PA43001, Amersham TM, Buckinghamshire, UK) and scanned with an Illumina bead array reader. Bead Studio 3.1.3.0 (Illumina Inc.) was used for signal extraction, quality control, and quantile normalization.

Computational Analysis of Microarray Data 6

The resulting data set was log-transformed and an unsupervised analysis with GO analysis software EGON (30) was performed. Further, the gene set analysis tool SAM-GS (Significance Analysis of Microarrays for Gene Sets), a method based on the SAM t-like statistics (31), was utilized for a supervised gene set analysis on eleven chosen gene sets comprising hypoxia, proliferation, wound healing and radiation resistance.

Statistics

Spearman correlation analysis was used to find genes that correlated with the A-parameter based on the Illumina data on the 46 DCE-MRI patients. Cox regression analysis identified the most important genes for progression free survival among the 109 patients in the validation group. Kaplan-Meier curves were compared using log-rank test. P-values of <0.05 were considered significant.

Results

Identification of Prognostic DCE-MRI Parameter

It was previously shown that the DCE-MRI parameter ABrix is a prognostic factor in cervical cancer where patients with low levels did significantly worse than those with high levels of $A_{Brix}$. The survival analysis was performed on each percentile of the parameter to show the robustness of the parameter, and to demonstrate which percentiles were more prognostic.

Figure 2:
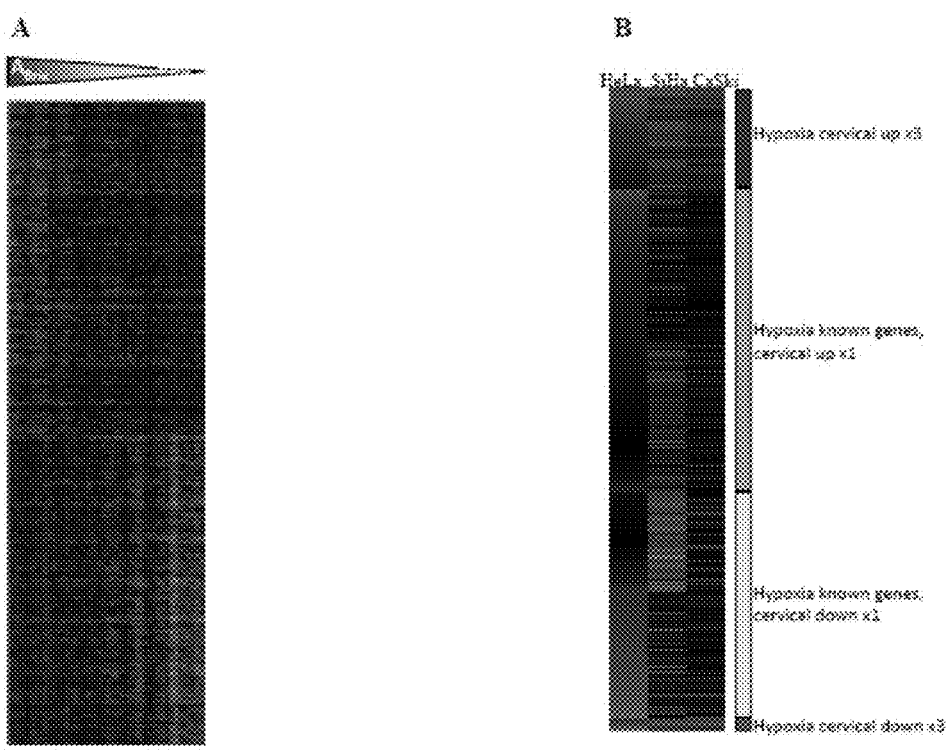
FIGS. 2 A, B, C and D provide depictions (heat maps and graphical) of gene expression in patients with cervical cancer.
Figure 2:
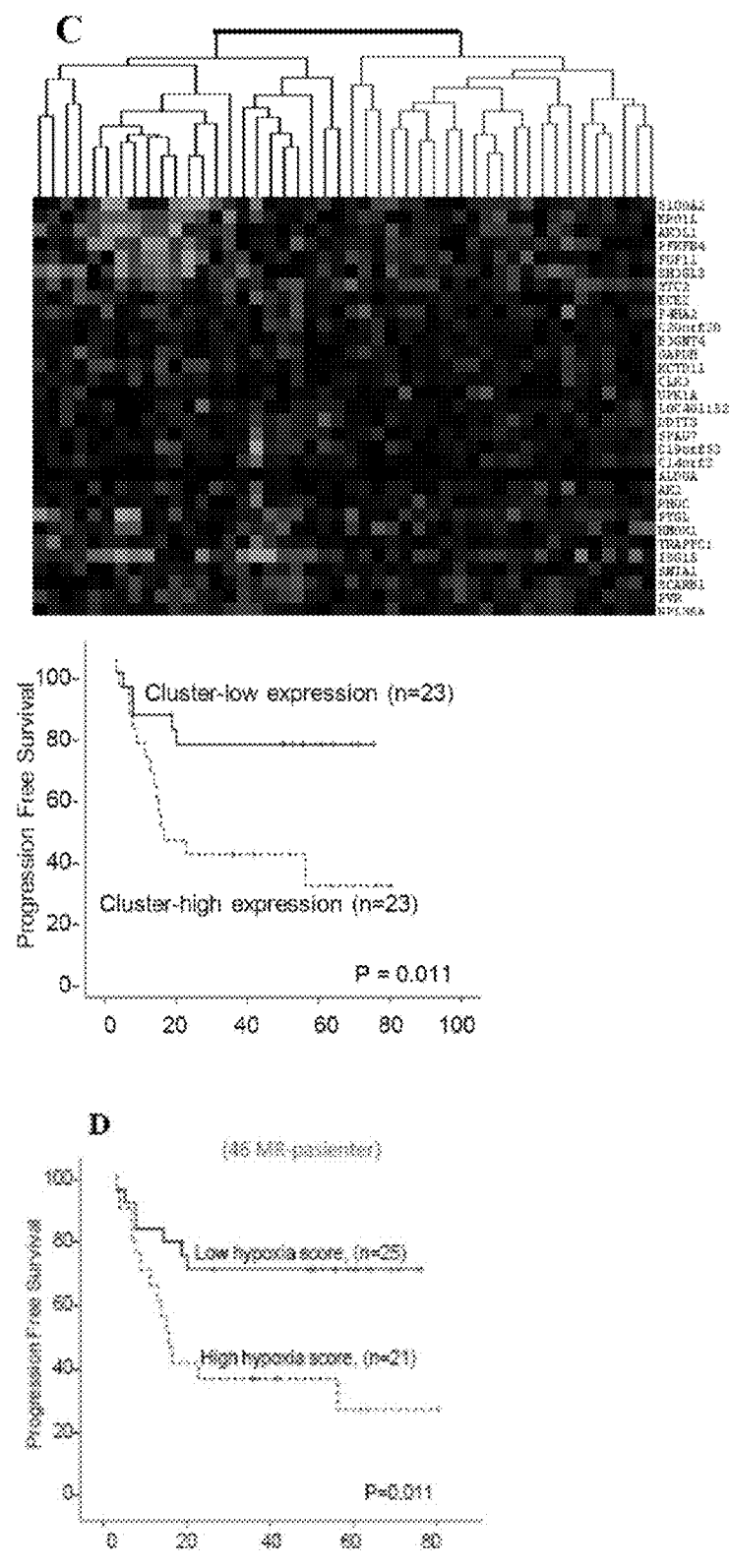

To explore the biological background of $A_{Brix}$, we chose one of the regions of the percentiles which was most significant (p=0.004) in relation to survival, namely the 20-30 percentile (FIG. 1b-c). Within these percentiles, $A_{Brix}$ differed among the patients, ranging from 0.59 to 3.21. The gene expression associated with ABrix was identified. It was found that 3714 Unigene probes corresponding to 3490 unique genes were correlated with ABrix (p<0.05) (FIG. 2a). Differences in the DCE-MR images were thus reflected in the transcriptional program of the tumors.

GO Analysis of DCE-MRI Correlating Gene

The genes which expressions were associated with ABrix were subjected to unsupervised GO analysis to find biological processes overrepresented in the tumors with a low value of ABrix. One or more biological processes were annotated to 1657 of the correlating genes and to 13650 of all genes in the array. Three major significant processes were identified; metabolism, cell cycle, and cellular component organization and biosynthesis, for which the metabolism category contained subgroups such as "one-carbon compound metabolism", "biopolymer metabolism", and "nucleobase, nucleoside, nucleotide and nucleic acid metabolic process" (Table 1). This suggests that ABrix reflects deregulation of metabolism and possibly increased cell growth and proliferation.

Since the GO analysis relies entirely on the annotation of the genes, we wanted to perform an analysis where annotation was not involved, to gain further insight into the biological functions of the genes that correlated with ABrix (negatively or positively). Thus, a supervised gene set enrichment analysis was performed, comparing two groups of tumors with ABrix values above and below the median, respectively. The analysis included gene sets from the literature reflecting the phenotypes hypoxia, proliferation, wound healing, and radioresistance, based on the knowledge from the EGON analysis. Only the hypoxia gene sets were found to be significantly enriched in the list of correlating genes (p=0.024 and p=0.031; data not shown), suggesting that hypoxia was the most significant phenotype reflected in the correlating genes.

To further improve the analysis we generated a cervical specific hypoxia gene list from cervical cancer cell lines grown under hypoxic conditions (0.2% O2, 24 h). HIF1α protein was induced in all three cell lines during the hypoxia treatment (Data not shown). The cell cycle distribution of the cells was not altered after the hypoxia treatment (Supplementary FIG. 1B), implying that the observed changes in gene expression were not a reflection of cell cycle perturbations, but rather a result of a true hypoxia response. Four different gene lists were generated; genes upregulated in all three cell lines, genes upregulated in one of the cell lines and confirmed by the literature, and correspondingly for the downregulated genes (FIG. 2b). The cervical cancer specific hypoxia gene lists were found to be the most significant in the subsequent gene set enrichment analysis (Table 2), indicating that DCE-MRI may be used to detect hypoxia in patients.

TABLE 1

Biological processes enriched in genes correlating with $A_{Brix}$ determined form GO analysis.

| GO acc. no. | GO term | Total size | Size | p-value |
|---|---|---|---|---|
| 0008150 | Biological process | 13650 | 1657 | |
| 0008152 | Metabolic process | 7809 | 1010 | 0.001 |
| 0006139 | Nucleobase++ metabolism | 3541 | 489 | <0.001 |
| 0006464 | Protein modification process | 1342 | 194 | 0.007 |
| 0006730 | One-carbon compound metabolism | 84 | 17 | 0.015 |
| 0043284 | Biopolymer metabolic process | 4783 | 661 | <0.001 |
| 0007049 | Cell cycle | 796 | 117 | 0.025 |
| 0016043 | Cellular component organization and biogenesis | 2238 | 304 | 0.023 |
| 0006996 | Organelle organization and biogenesis | 1148 | 166 | 0.014 |
| 0051276 | Chromosome organization and biogenesis | 373 | 66 | 0.002 |
| 0006974 | Response to DNA damage stimulus | 319 | 53 | 0.019 |

TABLE 2

Gene sets enriched in the list of correlating genes at determined by gene set enrichment analysis

| Gene set | Size? | p-value | Adj p-value |
|---|---|---|---|
| Hypoxia cervical up x3 | 79 | 0.008 | 0.085 |
| Hypoxia cervical up & literature | 286 | 0.020 | 0.085 |
| Hypoxia up (in vitro) (49) | 95 | 0.024 | 0.085 |
| Hypoxia up (in vitro) (50) | 91 | 0.031 | 0.085 |
| Hypoxia cervical down & literature | 183 | 0.072 | 0.158 |
| Wound heating (51) | 413 | 0.099 | 0.182 |
| Proliferation (52)* | 136 | 0.131 | 0.206 |
| Proliferation (51) | 104 | 0.172 | 0.226 |
| Hypoxia cervical down x3 | 10 | 0.185 | 0.226 |
| Radiation resistance (53) | 25 | 0.264 | 0.291 |
| Radiation resistance (54)* | 17 | 0.591 | 0.591 |

*From the Molecular Signatures Database (MSigDB) v3.0: http://www.broadinstinote.org/gsea/msigdb/ index.jsp
NOTE:
Gene sets in red color were created from cell line studies in our laboratory, while the remaining gene sets were taken from relevant literature or from the MSigDB Gene Signature Associated with the Prognostic DCE-MRI Parameters Based on the significant hypoxia gene sets we selected all the genes that that showed an inverse correlation between the expression of the gene and ABrix; i.e. those that were upregulated in tumors with low ABrix, representing a "DCE-MRI hypoxia signature". This signature consisted of 31 genes, listed in Table 3 together with the correlation coefficient and p-value for the relationship to ABrix. Many of the genes in the signature participated in biological processes known to be affected by hypoxia, such as energy metabolism, cell cycle, and proliferation (Table 3).

To ensure that the signature had prognostic impact in the DCE-MRI patients, we performed unsupervised clustering of the patients based on the gene expression levels of the 31 genes. Clustering showed two groups with different outcome (FIG. 2c). We further defined a DCE-MRI-hypoxia score for each tumor by averaging the median centered gene expression levels (converted to logarithmic scale) for these 31 genes, as described by Chi et al (32). In a Kaplan Meier survival analysis on the 46 DCE-MRI patients, this DCE-MRI-hypoxia score was significantly associated with survival (PFS; p=0.011) (FIG. 2d).

Multivariate Cox analysis was employed to find whether any individual genes were associated with clinical outcome. Only one gene emerged from this analysis, namely stanniocalcin 2 (STC2) with a p-values of 0.010 (Bckwd).(with Hazard ratios of 1.9). STC2 was strongly negatively correlated with A (p=0.007) and was up-regulated in all three cervical cell lines in response to hypoxia (HeLa: 2.5×, SiHa: 4.4×, CaSki: 2.8×). A Kaplan Meier analysis of STC2 showed that patients with a very high expression of STC2 did dramatically worse than patients with low STC2 expression (p=0.006).

TABLE 3

The DCE-MRI hypoxia gene signature

| Biological process* | Gene symbol | Gene name | Illumina ProbeID | p-value (low A) | Kore. Value |
|---|---|---|---|---|---|
| Metabolism | ALDOA | aldolase A, fructose-biphosphate | ILMN_1681374 | 0.028 | −0.307 |
|  | AX2 | adenylate kinase 2 | ILMN_1670542 | 0.038 | −0.306 |
|  | AK3L1 | adenylate kinase 4 | ILMN_2328038 | 0.010 | −0.328 |
|  | B3GNT4 | UDP-GlcNAcbetaGcl beta-1,3-N-acetylglucoamintransferase 4 | ILMN_1771268 | 0.504 | −0.416 |
|  | SCARB1 | scavenger receptor clan B, member 1 | ILMN_2183409 | 0.003 | −0.324 |
|  | CLK3 | CDC-like kinase 3 | ILMN_2320386 | 0.046 | −0.295 |
|  | CMORF20 | chromosome 20 open coading frame 20 | ILMN_1790136 | 0.017 | −0.350 |
|  | ECE2 | endothelim coverting enzyme 2 | ILMN_1762883 | 0.017 | −0.351 |
|  | ERO1L | ERO1-like (S. cerevisiae) | ILMN_1744963 | 0.019 | −0.345 |
|  | GAPDH | glycoaldehyde-3-phosphate dehydrogenase | ILMN_1802252 | 0.541 | −0.302 |
|  | HMOK1 | Homo oxygenase(decycling) | ILMN_1800512 | 0.024 | −0.335 |
|  | ISG15 | ISG15 obquitin-like modifier | ILMN_2054019 | 0.028 | −0.308 |
|  | PFKFB4 | 6-phosphofructo-2-kinase-fructose-2,8-biphosphatase 4 | ILMN_1658292 | 0.015 | −0.311 |
|  | P4HA2 | preiyl 4-hydroxylase, alpha polypeptide II | ILMN_2381697 | 0.050 | −0.291 |
|  | PYGL | phospholylase glycogen, lives | ILMN_1696187 | 0.011 | −0.371 |
|  | EPL36A | ribosomal protein L36a | ILMN_2112811 | 0.041 | −0.302 |
|  | UPK1A | uroplakin 1A | ILMN_1658637 | 0.008 | −0.285 |
| Cell cycle | DDIT3 | DNA-caroage-inducible transcript 3 | ILMN_1678834 | 0.004 | −0.414 |
|  | KCIDI1 | potassium channel tetramensation domain containing I1 | ILMN_1777513 | 0.022 | −0.328 |
|  | PVR | poliovirus receptor | ILMN_1677306 | 0.047 | −0.295 |
| Growth/hypoxia | KHOC | ras homolog gene family, member C | ILMN_1673305 | 0.043 | −0.299 |
| Proliferation/hypoxia | STC2 | 2 | ILMN_1691884 | 0.507 | −0.390 |
| Other/Unknown | C14OEF2 | chromosome 14 open reading frame 2 | ILMN_1652722 | 0.530 | −0.321 |
|  | C19OEF58 | chromosome 19 open reading frame 58 | ILMN_1671374 | 0.517 | −0.352 |
|  | C40EF3 | chromosome 4 open reading frame 3 | ILMN_2053684 | 0.049 | −0.292 |
|  | FGF11 | fibroblast growth fractor 11 | ILMN_1719838 | 0.023 | −0.316 |
|  | SH3GL3 | 5H5-domain GR52-like 3 | ILMN_1760990 | 0.038 | −0.307 |
|  | SNTA1 | syntrophia alpha 1 (dystrophin-associated protein A1, 59kDa, acid component) | ILMN_1753241 | 0.012 | −0.356 |
|  | SPAG7 | span associated antigen 7 | ILMN_1684446 | 0.011 | −0.372 |
|  | S100A2 | S100 calcium binding protein A2 | ILMN_1725852 | 0.009 | −0.381 |
|  | TRAFEC1 | trafficking protein particle complex 1 | ILMN_1716013 | 0.008 | −0.384 |

Validation in an Independent Cohort

Figure 3:
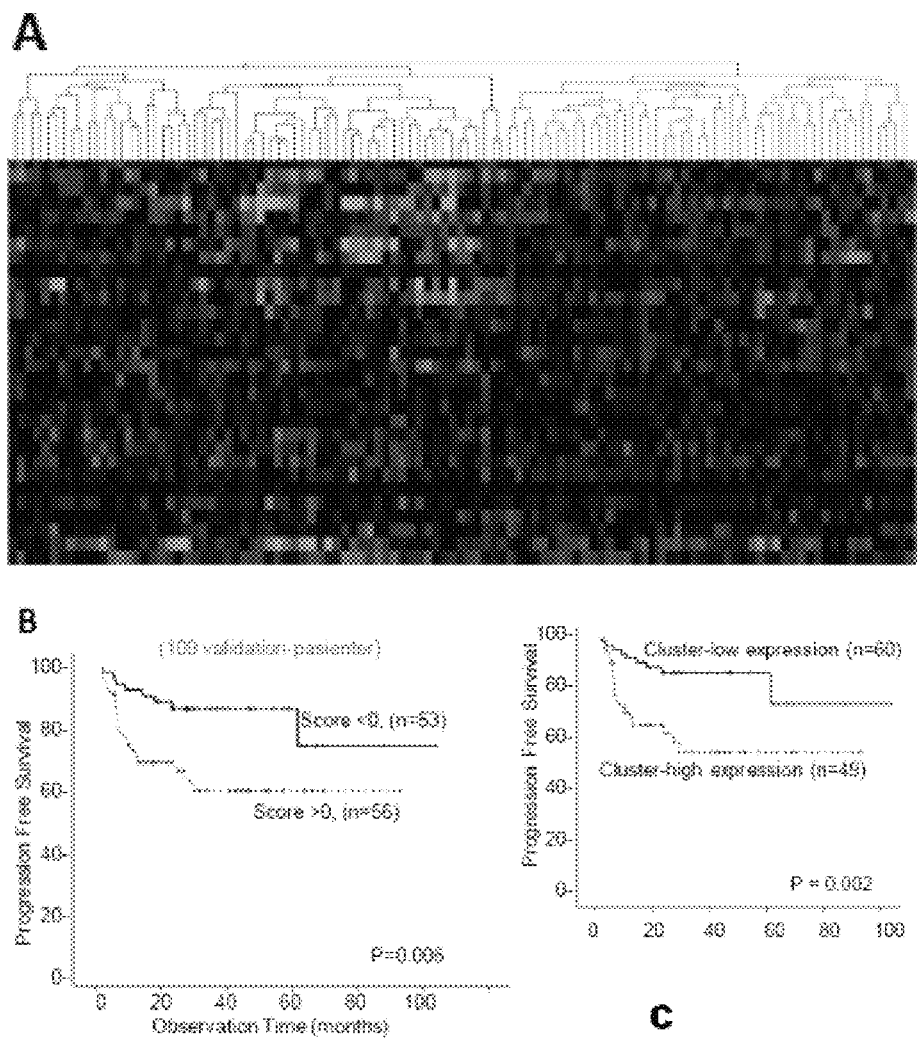
FIGS. 3 A, B and C provide depictions (heat maps and graphical) of gene expression in patients with cervical cancer.

To validate the prognostic impact of the DCE-MRI-hypoxia profile, a similar survival analysis was performed on an independent set of 109 cervical cancer patients. In the validation set, the clustering led to two different clusters, and the patients who clustered together due to high expression of the genes in the profile did significantly worse than the remaining patients (p=0.002) (FIG. 3a).

When assessing the DCE-MRI-hypoxia score in this independent cohort, the patients with a high score did significantly worse than the patients with a low score (p=0.006) (FIG. 3b), confirming the prognostic value of the DCE-MRI-hypoxia score.

STC2 was strongly negatively correlated with A (p=0.007; Table 3) and was up-regulated in all three cervical cell lines in response to hypoxia both on the transcriptional level (HeLa: 2.5×, SiHa: 4.4×, CaSki: 2.8×) and protein level.

Multivariate Cox analysis was employed to investigate the prognostic value of the DCE-MRI hypoxia score in relation to other clinical parameters in the cervical cancer patients, and it emerged as the only prognostic factor independent of lymph node status, FIGO stage, and tumor volume in the validation cohort of 109 patients (Table 4).

TABLE 4

Multivariate analysis of the DCE-MRI hypoxia score in the 109 validation patients.

| Factor | Univariate analysis | | | Multivariate analysis | | |
|---|---|---|---|---|---|---|
| | P | Hazard | 95% CI | P | Hazard ratio | 95% CI |
| Independent cohort patients | | | | | | |
| Progression Free Survival | | | | | | |
| Lymph nodes | 0.028 | 2.35 | 1.10-5.03 | N.S. | — | — |
| Tumor vol* | 0.021 | 2.70 | 1.16-6.29 | N.S. | — | — |
| FIGO-stage | 0.010 | 2.72 | 1.27-5.81 | (0.051) | 2.32 | 0.99-5.42 |
| DCE-MRI-Hypoxia-score (<0>) | 0.009 | 3.00 | 1.32-6.83 | 0.009 | 3.23 | 1.34-7.81 |

FIGO, the International Federation of Gynecology and Obstetrics
*Determined from the pre-treatment magnetic resonance images and calculated based on 3 orthogonal diameters (a, b, c) as $(\pi/6)$ abc.

Example 2

Figure 4:
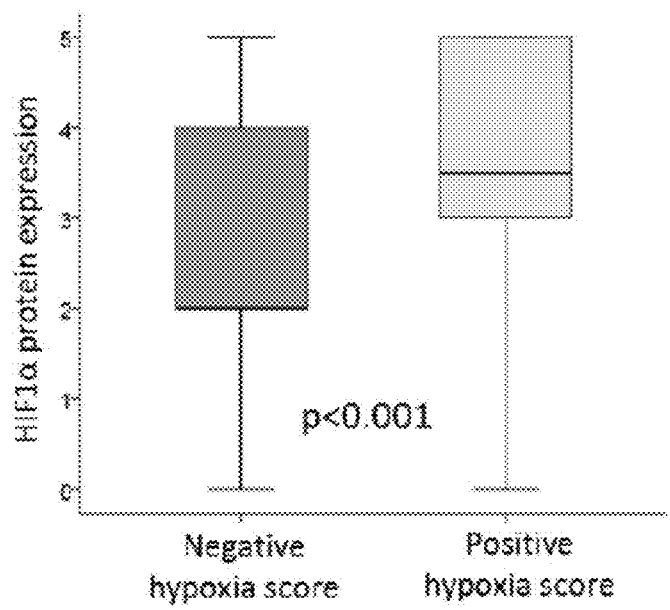
FIG. 4 provides a box plot (median, first, and third quartile) showing the distribution of HIF1α protein expression in patients with a negative (n=65) and positive (n=74) hypoxia score, respectively. The whiskers extend to the farthest points that are not outliers. P-value from Mann-Whitney U test.

Examination of the 31-gene hypoxia signature revealed that as many as eight of the genes are known target genes of HIF1α, which is a master regulator of the hypoxia response in cells. Based on this observation, it was determined to examine the role of HIF1α for the aggressive phenotype associated with the gene signature. Thus, immunohistochemistry experiments were performed to examine at the expression level of the HIF1α protein in all of the cervical tumors in our study. It was found that the level of HIF1α protein was significantly higher in the patients with a positive hypoxia score as calculated from our hypoxia gene signature, compared to the patients with a negative score (p<0.001) (FIG. 4). Furthermore, there was an individual correlation between HIF1α and the expression level of several of the 31 genes in the signature, including 5 of the 8 known HIF1α target genes (Table 5).

TABLE 5

Hypoxia signature genes and correlation with HIF1α

| Gene* | Corr. Coeff.** | p-value** |
|---|---|---|
| AK3L1 (AK4) | 0.397 | <0.001 |
| C20orf20 | 0.219 | 0.010 |
| ECE2 | 0.271 | 0.001 |
| ERO1L | 0.215 | 0.011 |
| FGF11 | 0.238 | 0.005 |
| GAPDH | 0.322 | <0.001 |
| KCTD11 | 0.196 | 0.020 |
| LOC401152 (C3orf4) | 0.197 | 0.020 |
| P4HA2 | 0.257 | 0.002 |
| PFKFB4 | 0.369 | <0.001 |
| PVR | 0.272 | 0.001 |
| RPL36A | 0.163 | 0.056 |
| STC2 | 0.156 | 0.067 |
| TRAPPC1 | 0.214 | 0.011 |

*Genes in bold are known targets of the HIF1α protein
**Correlation coefficient and p-value from Spearman's rank correlation.

These findings indicate that HIF1α is activated in tumors with a high expression of the genes in our signature, and supports the association between our gene signature and a hypoxic phenotype.

Example 3

The following example provides data showing superior prognostic value of the gene signature in lymph node negative patients.

Comparison Between Lymph Node Negative and Positive Patients

Figure 5:
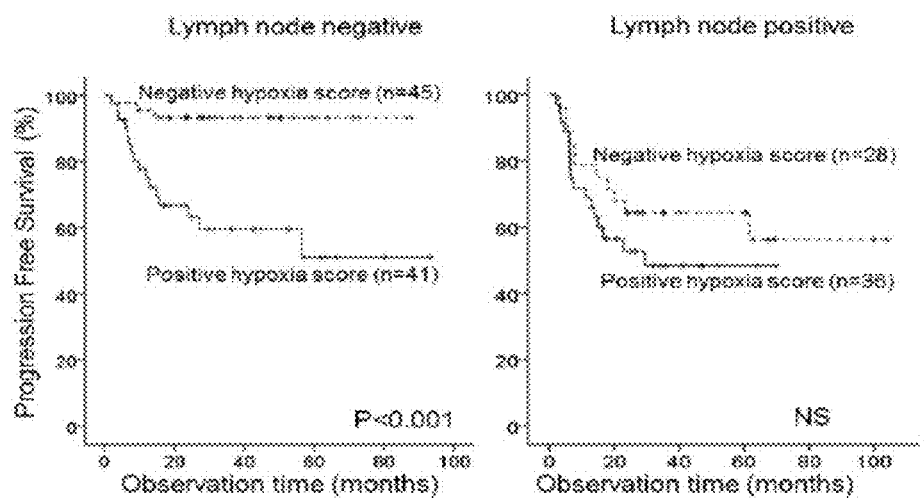
FIG. 5 provides Kaplan-Meier curves for progression-free survival of patients with negative (dotted) and positive (solid) hypoxia score in lymph node negative (left) and positive (right) patients. P values from log-rank test and number of patients are indicated in the Kaplan-Meier plots.

The data above shows the excellent prognostic value of the 31-gene hypoxia signature in locally advanced cervical cancer. We further investigated the issue of whether the signature had a different prognostic value for different subgroups of the patients. Patients were stratified based on the presence of lymph node metastases, before performing a Kaplan Meier survival analysis. This analysis showed that the signature was strongly associated with poor outcome for the patients without metastases to the lymph nodes (p<0.001) (FIG. 5). In this patient group, the probability of progression free survival decreased from 93.3% to 51% for the patients with a positive hypoxia score. In the lymph node positive patients, there was a tendency towards an association between the hypoxia score and outcome (FIG. 5), but the number of patients was probably too low to obtain statistical significance.

Comparison Between the Gene Signature and HIF1α Protein Expression

Figure 6:
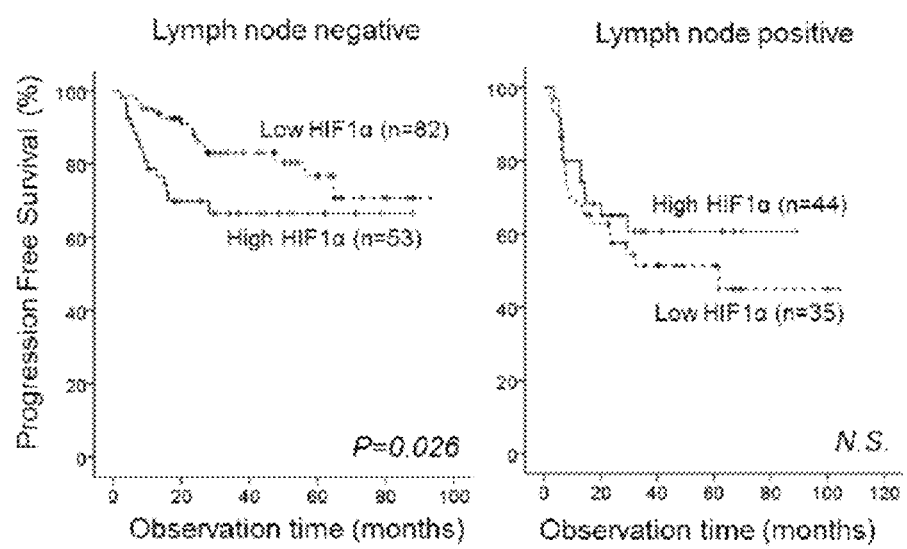
FIG. 6 provides Kaplan-Meier curves for progression-free survival (right) of patients with low (dotted) and high (solid) expression of HIF1α in lymph node negative (left) and positive (right) patients. P-values from log-rank test and number of patients are indicated in the Kaplan-Meier plots.

HIF1α protein expression has been proposed as a hypoxia marker due to its role in the cellular hypoxia response. We therefore compared the prognostic impact of our gene signature with the impact of HIF1α protein expression in our cohort of cervical cancer. It was found that HIF1α protein expression was not correlated with survival. However, in concordance with the finding for the hypoxia score; in patients with no lymph node metastases, high levels of HIF1α appeared as a significant prognostic indicator of poor outcome (p=0.026) (FIG. 6).

From the Kaplan-Meier analysis, HIF1α protein expression seemed to have a weaker prognostic impact than the hypoxia score. To evaluate the relative importance of the hypoxia score and HIF1α protein expression for the survival of the patients, a multivariate Cox analysis of these factors together with clinical parameters was performed in the patient group with no lymph node metastases (n=86). Only the hypoxia score and FIGO stage were found to be independently related to patient survival from this analysis (Table 6).

TABLE 6

Cox regression analysis of the hypoxia score, HIF1α and clinical variables and progression free survival in the 86 lymph node negative patients

| Factor | Univariate analysis | | | Multivariate analysis | | |
|---|---|---|---|---|---|---|
|  | P | Relative Risk | 95% CI | P | Relative Risk | 95% CI |
| Tumor volume[a] | 0.018 | 3.51 | 1.24-9.99 | N.S. | — | — |
| FIGO-stage[b] | 0.028 | 2.79 | 1.12-6.95 | 0.042 | 2.83 | 1.03-7.70 |
| Hypoxia-score[c] | 0.002 | 7.21 | 2.10-24.77 | 0.003 | 9.50 | 2.15-41.90 |
| HIF1α[d] | 0.059 | 2.39 | 0.97-5.91 | N.S | — | — |

Abbreviations: FIGO. Federation International de Gynecologie et d'Obstetrique: P. P-value; CI. confidence interval
[a]Tumor size was divided into two groups on the basis of the median volume of 43.8 cm$^3$;
[b]FIGO stage was divided into two groups: 1b-2b and 3a-4a;
[c]The hypoxia score was divided into two groups, based on values <0 and >0.
[d]The HIF1α immunohistochemistry score was divided into 2 groups: 0-3, 4-5

CONCLUSION

The data presented above indicates that HIF1α, which is used as a marker of hypoxia in certain cancer types, is an important mediator of the aggressive phenotype associated with our hypoxia gene signature. This supports the connection between the 31-gene hypoxia signature and a hypoxic phenotype. The multivariate analysis showed that the hypoxia signature was a significantly better prognostic factor than HIF1α. Moreover, the gene signature seems to be associated with aggressiveness particularly in patients with no metastases to the lymph nodes. This patient group typically constitutes the major subgroup of cervical cancer patients subjected to curative chemoradiotherapy. There are few means of identifying patients in this subgroup with a high risk of relapse, and interestingly, hypoxia has been shown to be among the strongest prognostic factors for these patients (55). This data shows that the hypoxia gene signature is a needed biomarker for identifying patients with hypoxia-related chemoradioresistance in this patient group.

REFERENCE LIST (1) Coleman C N. Linking radiation oncology and imaging through molecular biology (or now that therapy and diagnosis have separated, it's time to get together again!). Radiology 2003; 228:29-35.
(2) Balleyguier C, Sala E, Da C T, Bergman A, Brkljacic B, Danza F, et al. Staging of uterine cervical cancer with MRI: guidelines of the European Society of Urogenital Radiology. Eur Radiol 2010.
(3) Follen M, Levenback C F, Iyer R B, Grigsby P W, Boss E A, Delpassand E S, et al. Imaging in cervical cancer. Cancer 2003; 98:2028-38.
(4) Potter R, Dimopoulos J, Georg P, Lang S, Waldhausl C, Wachter-Gerstner N, et al. Clinical impact of MRI assisted dose volume adaptation and dose escalation in brachytherapy of locally advanced cervix cancer. Radiother Oncol 2007; 83:148-55.
(5) De B M, Mousa A G, Nulens A, Swinnen A, Van L E. Potential of dose optimisation in MRI-based PDR brachytherapy of cervix carcinoma. Radiother Oncol 2008; 88:217-26.
(6) Loncaster J A, Carrington B M, Sykes J R, Jones A P, Todd S M, Cooper R, et al. Prediction of radiotherapy outcome using dynamic contrast enhanced MRI of carcinoma of the cervix. Int J Radiat Oncol Biol Phys 2002; 54:759-67.
(7) Hawighorst H, Weikel W, Knapstein P G, Knopp M V, Zuna I, Schonberg S O, et al. Angiogenic activity of cervical carcinoma: assessment by functional magnetic resonance imaging-based parameters and a histomorphological approach in correlation with disease outcome. Clin Cancer Res 1998; 4:2305-12.
(8) Mayr N A, Yuh W T C, Arnholt J C, Ehrhardt J C, Sorosky J I, Magnotta V A, et al. Pixel analysis of MR perfusion imaging in predicting radiation therapy outcome in cervical cancer. Magn Reson Imaging 2000; 12:1027-33.
(9) Gong Q Y, Brunt J N, Romaniuk C S, Oakley J P, Tan L T, Roberts N, et al. Contrast enhanced dynamic MRI of cervical carcinoma during radiotherapy: early prediction of tumour regression rate. Br J Radiol 1999; 72:1177-84.
(10) Yamashita Y, Baba T, Baba Y, Nishimura R, Ikeda S, Takahashi M, et al. Dynamic contrast-enhanced MR imaging of uterine cervical cancer: pharmacokinetic analysis with histopathologic correlation and its importance in predicting the outcome of radiation therapy. Radiology 2000; 216:803-9.
(11) Yuh W T, Mayr N A, Jarjoura D, Wu D, Grecula J C, Lo S S, et al. Predicting control of primary tumor and survival by DCE MRI during early therapy in cervical cancer. Invest Radiol 2009; 44:343-50.
(12) Andersen E K, Hole K H, Lund K V, Sundfor K, Kristensen G B, Lyng H, et al. Dynamic Contrast-Enhanced MRI of Cervical Cancers: Temporal Percentile Screening of Contrast Enhancement Identifies Parameters for Prediction of Chemoradioresistance. Int J Radiat Oncol Biol Phys 2011.
(13) Tofts P S. Modeling tracer kinetics in dynamic Gd-DTPA MR imaging. J Magn Reson Imaging 1997; 7:91-101.
(14) Brix G, Semmler W, Port R, Schad L R, Layer G, Lorenz W J. Pharmacokinetic parameters in CNS Gd-DTPA enhanced MR imaging. J Comput Assist Tomogr 1991; 15:621-8.
(15) Barajas R F, Jr., Hodgson J G, Chang J S, Vandenberg S R, Yeh R F, Parsa A T, et al. Glioblastoma multiforme regional genetic and cellular expression patterns: influence on anatomic and physiologic MR imaging. Radiology 2010; 254:564-76.
(16) Costouros N G, Lorang D, Zhang Y, Miller M S, Diehn F E, Hewitt S M, et al. Microarray gene expression analysis of murine tumor heterogeneity defined by dynamic contrast-enhanced MRI. Mol Imaging 2002; 1:301-8.

(17) Diehn M, Nardini C, Wang D S, McGovern S, Jayaraman M, Liang Y, et al. Identification of noninvasive imaging surrogates for brain tumor gene-expression modules. Proc Natl Acad Sci USA 2008; 105:5213-8.

(18) Pope W B, Chen J H, Dong J, Carlson M R, Perlina A, Cloughesy T F, et al. Relationship between gene expression and enhancement in glioblastoma multiforme: exploratory DNA microarray analysis. Radiology 2008; 249:268-77.

(19) Yang Y S, Guccione S, Bednarski M D. Comparing genomic and histologic correlations to radiographic changes in tumors: a murine SCC VII model study. Acad Radiol 2003; 10:1165-75.

(20) Zinn P O, Majadan B, Sathyan P, Singh S K, Majumder S, Jolesz F A, et al. Radiogenomic Mapping of Edema/Cellular Invasion MRI-Phenotypes in Glioblastoma Multiforme. PLoS One 2011; 6:e25451.

(21) Lenkinski R E, Bloch B N, Liu F, Frangioni T V, Perner S, Rubin M A, et al. An illustration of the potential for mapping MRI/MRS parameters with genetic over-expression profiles in human prostate cancer. MAGMA 2008; 21:411-21.

(22) Lyng H, Brovig R S, Svendsrud D H, Holm R, Kaalhus O, Knutstad K, et al. Gene expressions and copy numbers associated with metastatic phenotypes of uterine cervical cancer. BMC Genomics 2006; 7:268.

(23) van Persijn van Meerten E L, Gelderblom H, Bloem J L. RECIST revised: implications for the radiologist. A review article on the modified RECIST guideline. Eur Radiol 2010; 20:1456-67.

(24) Markwardt C B. Non-linear least squares fitting in IDL with MPFIT. In Proceedings of the Astronomical data analysis software and systems XVIII, eds. D. Bohlender, P. Dowler and D. Durand. Quebec, Canada 2008 p. 411: 251-254.

(25) Tofts P S. Modeling tracer kinetics in dynamic Gd-DTPA MR imaging. J Magn Reson Imaging 1997; 7:91-101.

(26) Huang L E, Arany Z, Livingston D M, Bunn H F. Activation of hypoxia-inducible transcription factor depends primarily upon redox-sensitive stabilization of its alpha subunit. Biol Chem 1996; 271:32253-9.

(27) Koumenis C, Wouters B G. "Translating" tumor hypoxia: unfolded protein response (UPR)-dependent and UPR-independent pathways. Mol Cancer Res 2006; 4:423-36.

(28) Lando M, Holden M, Bergersen L C, Svendsrud D H, Stokke T, Sundfor K, et al. Gene dosage, expression, and ontology analysis identifies driver genes in the carcinogenesis and chemoradioresistance of cervical cancer. PLoS Genet 2009; 5:e1000719.

(29) Lyng H, Landsverk K S, Kristiansen E, DeAngelis P M, Ree A H, Myklebost O, et al. Response of malignant B lymphocytes to ionizing radiation: gene expression and genotype. Int J Cancer 2005; 115:935-42.

(30) Beisvag V, Junge F K, Bergum H, Jolsum L, Lydersen S, Gunther C C, et al. GeneTools—application for functional annotation and statistical hypothesis testing. BMC Bioinformatics 2006; 7:470.

(31) Dinu I, Potter J D, Mueller T, Liu Q, Adewale A J, Jhangri G S, et al. Improving gene set analysis of microarray data by SAM-GS. BMC Bioinformatics 2007; 8:242.: 242.

(32) Chi J T, Wang Z, Nuyten D S, Rodriguez E H, Schaner M E, Salim A, et al. Gene expression programs in response to hypoxia: cell type specificity and prognostic significance in human cancers. PLoS Med 2006; 3:e47.

(33) Hagtvet E, Roe K, Olsen D R. Liposomal doxorubicin improves radiotherapy response in hypoxic prostate cancer xenografts. Radiat Oncol 2011; 6:135.:135.

(34) Hockel M, Schlenger K, Aral B, Mitze M, Schaffer U, Vaupel P. Association between tumor hypoxia and malignant progression in advanced cancer of the uterine cervix. Cancer Res 1996; 56:4509-15.

(35) Gharib T G, Chen G, Huang C C, Misek D E, Iannettoni M D, Hanash S M, et al. Genomic and proteomic analyses of vascular endothelial growth factor and insulin-like growth factor-binding protein 3 in lung adenocarcinomas. Clin Lung Cancer 2004; 5:307-12.

(36) Ewing R M, Chu P, Elisma F, Li H, Taylor P, Climie S, et al. Large-scale mapping of human protein-protein interactions by mass spectrometry. Mol Syst Biol 2007; 3:89. Epub; %2007 Mar. 13.:89.

(37) Schodel J, Oikonomopoulos S, Ragoussis J, Pugh C W, Ratcliffe P J, Mole D R. High-resolution genome-wide mapping of HIF-binding sites by ChIP-seq. Blood 2011; 117:e207-e217.

(38) Burkart A, Shi X, Chouinard M, Corvera S. Adenylate kinase 2 links mitochondrial energy metabolism to the induction of the unfolded protein response. J Biol Chem 2011; 286:4081-9.

(39) Feldman D E, Chauhan V, Koong A C. The unfolded protein response: a novel component of the hypoxic stress response in tumors. Mol Cancer Res 2005; 3:597-605.

(40) Ito D, Walker J R, Thompson C S, Moroz I, Lin W, Veselits M L, et al. Characterization of stanniocalcin 2, a novel target of the mammalian unfolded protein response with cytoprotective properties. Mol Cell Biol 2004; 24:9456-69.

(41) Meyer H A, Tolle A, Jung M, Fritzsche F R, Haendler B, Kristiansen I, et al. Identification of stanniocalcin 2 as prognostic marker in renal cell carcinoma. Eur Urol 2009; 55:669-78.

(42) Kita Y, Mimori K, Iwatsuki M, Yokobori T, Ieta K, Tanaka F, et al. STC2: a predictive marker for lymph node metastasis in esophageal squamous-cell carcinoma. Ann Surg Oncol 2011; 18:261-72.

(43) Yokobori T, Mimori K, Ishii H, Iwatsuki M, Tanaka F, Kamohara Y, et al. Clinical significance of stanniocalcin 2 as a prognostic marker in gastric cancer. Ann Surg Oncol 2010; 17:2601-7.

(44) Law A Y, Wong C K. Stanniocalcin-2 is a HIF-1 target gene that promotes cell proliferation in hypoxia. Exp Cell Res 2010; 316:466-76.

(45) Law A Y, Wong C K. Stanniocalcin-2 promotes epithelial-mesenchymal transition and invasiveness in hypoxic human ovarian cancer cells. Exp Cell Res 2010; 316:3425-34.

(46) Rouschop K M, van den Beucken T, Dubois L, Niessen H, Bussink J, Savelkouls K, et al. The unfolded protein response protects human tumor cells during hypoxia through regulation of the autophagy genes MAP1LC3B and ATG5. J Clin Invest 2010; 120:127-41.

(47) Hillengass J, Wasser K, Delorme S, Kiessling F, Zechmann C, Benner A, et al. Lumbar bone marrow microcirculation measurements from dynamic contrast-enhanced magnetic resonance imaging is a predictor of event-free survival in progressive multiple myeloma. Clin Cancer Res 2007; 13:475-81.

(48) Brix G, Semmler W, Port R, Schad L R, Layer G, Lorenz W J. Pharmacokinetic parameters in CNS Gd-DTPA enhanced MR imaging. J Comput Assist Tomogr 1991; 15:621-8.

(49) Mense S M, Sengupta A, Zhou M, Lan C, Bentsman G, Volsky D J, et al. Gene expression profiling reveals the profound upregulation of hypoxia-responsive genes in primary human astrocytes. Physiol Genomics 2006; 25:435-49.

(50) Winter S C, Buffa F M, Silva P, Miller C, Valentine H R, Turley H, et al. Relation of a hypoxia metagene derived from head and neck cancer to prognosis of multiple cancers. Cancer Res 2007; 67:3441-9.

(51) Starmans M H, Krishnapuram B, Steck H, Horlings H, Nuyten D S, Van d, V, et al. Robust prognostic value of a knowledge-based proliferation signature across large patient microarray studies spanning different cancer types. Br J Cancer 2008; 99:1884-90.

(52) Chiang D Y, Villanueva A, Hoshida Y, Peix J, Newell P, Minguez B, et al. Focal gains of VEGFA and molecular classification of hepatocellular carcinoma. Cancer Res 2008; 68:6779-88.

(53) Ishigami T, Uzawa K, Higo M, Nomura H, Saito K, Kato Y, et al. Genes and molecular pathways related to radioresistance of oral squamous cell carcinoma cells. Int J Cancer 2007; 120:2262-70. 19

(54) Amundson S A, Do K T, Vinikoor L C, Lee R A, Koch-Paiz C A, Ahn J, et al. Integrating global gene expression and radiation survival parameters across the 60 cell lines of the National Cancer Institute Anticancer Drug Screen. Cancer Res 2008; 68:415-24.

(55) Fyles, A. Tumor hypoxia has independent predictor impact only in patients with node-negative cervix cancer, 2002.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the medical sciences are intended to be within the scope of the following claims.

The invention claimed is:

1. A method for detectably labelling a set of gene products from a human biological sample comprising:
   contacting a cervical tumor sample from a subject with reagents for reverse transcribing at least three hypoxia profile gene products selected from the group consisting of ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1, mRNA transcripts to provide complementary DNA; and
   b) amplifying said complementary DNA in the presence of a probe to provide detectably labeled amplified complementary DNA.

2. The method of claim 1, wherein said patient hypoxia profile is further determined by measurement of the $A_{Brix}$ parameter using magnetic resonance imaging (MRI).

3. The method of claim 1, wherein said patient hypoxia profile is compared to a reference profile.

4. The method of claim 1, further comprising reverse transcribing, amplifying and detectably labeling at least five gene products selected from the group consisting of ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1 mRNA transcripts.

5. The method of claim 1, further comprising reverse transcribing, amplifying and detectably labeling at least ten gene products selected from the group consisting of ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1 mRNA transcripts.

6. The method of claim 1, further comprising reverse transcribing, amplifying and detectably labeling at least fifteen gene products at selected from the group consisting of ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1 mRNA transcripts.

7. The method of claim 1, further comprising reverse transcribing, amplifying and detectably labeling at least twenty gene products selected from the group consisting of ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1 mRNA transcripts.

8. The method of claim 1, further comprising reverse transcribing, amplifying and detectably labeling at least twenty-five gene products selected from the group consisting of ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1 mRNA transcripts.

9. The method of claim 1, further comprising reverse transcribing, amplifying and detectably labeling at least thirty gene products selected from the group consisting of ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1 mRNA transcripts.

10. The method of claim 1, further comprising reverse transcribing, amplifying and detectably labeling ALDOA, AK2, AK3L1, B3GNT4, SCARB1, CLK3, C20ORF20, ECE2, ERO1L, GAPDH, HMOX1, ISG15, PFKFB4, P4HA2, PYGL, RPL36A, UPK1A, DDIT3, KCTD11, PVR, RHOC, STC2, C14ORF2, C19ORF53, C4ORF3, FGF11, SH3GL3, SNTA1, SPAG7, S100A2 and TRAPPC1 mRNA transcripts.

11. The method of claim 1, wherein said altered level of expression of said gene products is expressed as a hypoxia score for a tumor.

12. The method of claim 11, wherein said hypoxia score is determined by averaging the median centered gene expression levels for said gene products.

13. The method of claim 1, wherein said subject is lymph node negative.

* * * * *